US012800836B2

(12) United States Patent
Hajati et al.

(10) Patent No.: US 12,800,836 B2
(45) Date of Patent: Nov. 17, 2026

(54) INTEGRATED ARRAYS FOR COHERENT OPTICAL DETECTION

(71) Applicant: LYTE AI, INC., Mountain View, CA (US)

(72) Inventors: Arman Hajati, San Carlos, CA (US); Yuval Gerson, Sunnyvale, CA (US); Alexander Shpunt, Saratoga, CA (US)

(73) Assignee: Lyte AI, Inc., Sunnyvale, CA (US)

( * ) Notice: Subject to any disclaimer, the term of this patent is extended or adjusted under 35 U.S.C. 154(b) by 238 days.

(21) Appl. No.: 18/683,260

(22) PCT Filed: Aug. 17, 2022

(86) PCT No.: PCT/US2022/040526
§ 371 (c)(1),
(2) Date: Feb. 13, 2024

(87) PCT Pub. No.: WO2023/023105
PCT Pub. Date: Feb. 23, 2023

(65) Prior Publication Data

US 2025/0138385 A1 May 1, 2025

Related U.S. Application Data

(60) Provisional application No. 63/342,176, filed on May 16, 2022, provisional application No. 63/240,012, (Continued)

(51) Int. Cl.
*G02B 6/28* (2006.01)
*G01S 7/481* (2006.01)
(Continued)

(52) U.S. Cl.
CPC .......... *G02B 6/2817* (2013.01); *G01S 7/4817* (2013.01); *G01S 17/34* (2020.01);
(Continued)

(58) Field of Classification Search
None
See application file for complete search history.

(56) References Cited

U.S. PATENT DOCUMENTS 5,442,720 A 8/1995 Shaw
8,593,711 B2 11/2013 Borchers et al.
(Continued)

FOREIGN PATENT DOCUMENTS

CA 3135485 A1 10/2020
CN 111722237 A 9/2020
(Continued)

OTHER PUBLICATIONS

International Appliction # PCT/US2022/40527 Search Report dated Feb. 3, 2023.

(Continued)

*Primary Examiner* — Jerry Rahll
(74) *Attorney, Agent, or Firm* — Meitar Patents LTD.; Daniel Kligler

(57) ABSTRACT

An optoelectronic device (20, 50, 120, 320, 500, 540, 560, 600) includes an array (32, 72, 124) of optical transceiver cells (34, 74, 90, 126, 522) disposed on a planar substrate (30). Each transceiver cell includes an optical transducer (36) configured to couple optical radiation between the transceiver cell and a target. An optical distribution tree (122) including a network (38, 76, 428, 518, 524) of waveguides (142, 150) and switches (146, 429), is disposed on the substrate and coupled to convey coherent radiation from a radiation source (52, 128, 130, 426, 510, 606) to the optical transceiver cells. A controller (48) is configured to actuate the switches so as to select different subsets of the optical transceiver cells that are to receive the coherent
(Continued)

radiation from the optical distribution tree and to transmit the coherent radiation toward the target at different times during a scan of the target.

24 Claims, 17 Drawing Sheets

Related U.S. Application Data filed on Sep. 2, 2021, provisional application No. 63/234,700, filed on Aug. 18, 2021.

(51) Int. Cl.

| | |
|---|---|
| ***G01S 17/34*** | (2020.01) |
| ***G01S 17/42*** | (2006.01) |
| ***G02B 6/02*** | (2006.01) |
| ***G02B 6/35*** | (2006.01) |
| ***G02F 1/31*** | (2006.01) |
| *A61B 3/10* | (2006.01) |
| *G02B 6/12* | (2006.01) |
| *G02B 6/42* | (2006.01) |

(52) U.S. Cl.

CPC ............ *G01S 17/42* (2013.01); *G02B 6/0208* (2013.01); *G02B 6/3588* (2013.01); *G02F 1/311* (2021.01); *A61B 3/102* (2013.01); *G01S 7/4814* (2013.01); *G01S 7/4815* (2013.01); *G01S 7/4816* (2013.01); *G02B 2006/1215* (2013.01); *G02B 6/2861* (2013.01); *G02B 6/356* (2013.01); *G02B 6/3562* (2013.01); *G02B 6/4286* (2013.01); *G02F 2203/70* (2013.01)

(56) References Cited

U.S. PATENT DOCUMENTS

| | | | | |
|---|---|---|---|---|
| 9,007,569 | B2 | 4/2015 | Amzajerdian et al. | |
| 9,683,928 | B2 | 6/2017 | Swanson | |
| 11,977,259 | B2 | 5/2024 | Hajati et al. | |
| 12,025,749 | B2 | 7/2024 | Asghari et al. | |
| 2002/0001870 | A1 | 1/2002 | Oda et al. | |
| 2002/0030094 | A1 | 3/2002 | Curry et al. | |
| 2004/0202418 | A1 | 10/2004 | Ghiron | |
| 2006/0079762 | A1 | 4/2006 | Norris et al. | |
| 2007/0177152 | A1 | 8/2007 | Tearney et al. | |
| 2008/0019693 | A1 | 1/2008 | Sorin | |
| 2008/0031583 | A1 | 2/2008 | Ohtsu et al. | |
| 2008/0167819 | A1 | 7/2008 | Breed | |
| 2009/0310118 | A1 | 12/2009 | Halldorsson | |
| 2010/0284696 | A1 | 11/2010 | Gao | |
| 2011/0134679 | A1 | 6/2011 | Suh et al. | |
| 2014/0276108 | A1 | 9/2014 | Vertikov | |
| 2014/0286605 | A1 | 9/2014 | Lee | |
| 2017/0067829 | A1* | 3/2017 | Duer | G01N 21/6452 |
| 2017/0299697 | A1 | 10/2017 | Swanson | |
| 2017/0314763 | A1 | 11/2017 | Petronius et al. | |
| 2017/0317750 | A1 | 11/2017 | Chaffee et al. | |
| 2018/0156600 | A1 | 6/2018 | Cable et al. | |
| 2018/0348434 | A1 | 12/2018 | Yim et al. | |
| 2019/0004247 | A1 | 1/2019 | Huang et al. | |
| 2019/0383913 | A1 | 12/2019 | Crouch et al. | |
| 2020/0003975 | A1 | 1/2020 | Yu et al. | |
| 2020/0076152 | A1 | 3/2020 | Eichenholz et al. | |
| 2020/0116837 | A1 | 4/2020 | Aghari et al. | |
| 2020/0116842 | A1 | 4/2020 | Aghari et al. | |
| 2020/0124711 | A1 | 4/2020 | Rezk et al. | |
| 2020/0132949 | A1 | 4/2020 | Huang et al. | |
| 2020/0158831 | A1 | 5/2020 | Niclass et al. | |
| 2020/0169056 | A1 | 5/2020 | Popovic et al. | |
| 2020/0174124 | A1 | 6/2020 | Raring et al. | |
| 2020/0284883 | A1 | 9/2020 | Ferreira et al. | |
| 2020/0284981 | A1 | 9/2020 | Harris et al. | |
| 2020/0301244 | A1 | 9/2020 | Wang | |
| 2021/0038280 | A1 | 2/2021 | Pikramenos | |
| 2021/0055694 | A1 | 2/2021 | Chan et al. | |
| 2021/0072384 | A1 | 3/2021 | Balbas | |
| 2021/0125975 | A1 | 4/2021 | Kang et al. | |
| 2021/0336422 | A1 | 10/2021 | Tan et al. | |
| 2021/0373157 | A1 | 12/2021 | Pierrottet et al. | |
| 2021/0373162 | A1* | 12/2021 | Wu | G01S 7/4818 |
| 2022/0011409 | A1 | 1/2022 | Hosseini et al. | |
| 2022/0236384 | A1 | 7/2022 | Sutton et al. | |
| 2024/0069285 | A1 | 2/2024 | Hajati et al. | |
| 2025/0138385 | A1 | 5/2025 | Hajati et al. | |

FOREIGN PATENT DOCUMENTS

| | | | |
|---|---|---|---|
| CN | 112292613 | A | 1/2021 |
| CN | 113227823 | A | 8/2021 |
| EP | 3961278 | A1 | 3/2022 |
| JP | 3461108 | B2 | 10/2003 |
| JP | 6696782 | B2 | 5/2020 |
| WO | 2016202709 | A1 | 12/2016 |
| WO | 2020083845 | A1 | 4/2020 |
| WO | 2020227761 | A1 | 11/2020 |
| WO | 2021029969 | A1 | 2/2021 |
| WO | 2021116766 | A1 | 6/2021 |
| WO | 2021150826 | A1 | 7/2021 |
| WO | 2022043949 | A1 | 3/2022 |
| WO | 2023023105 | A1 | 2/2023 |
| WO | 2023023106 | A2 | 2/2023 |
| WO | 2023034465 | A2 | 3/2023 |
| WO | 2023076132 | A1 | 5/2023 |

OTHER PUBLICATIONS

Xi et al., "Generic Real-time Uniform K-Space Sampling Method for High-speed Swept-source Optical Coherence Tomography," Optics Express, vol. 18, issue 9, pp. 1-7, Apr. 26, 2010.
International Application # PCT/US2022/040526 Search Report dated Jan. 18, 2023.
International Application # PCT/US23/77383 Search Report dated Mar. 13, 2024.
Noriki et al., "45-degree Curved Micro-mirror for Vertical Optical I/O of Silicon Photonics Chip," Optics Express, vol. 27, issue 14, pp. 19749-19757, year 2019.
Dai et al., "Novel Concept for Ultracompact Polarization Splitter-rotator Based on Silicon Nanowires," Optics Express, vol. 19, No. 11, pp. 10940-10949, year 2011.
Guan et al., "CMOS-compatible Highly Efficient Polarization Splitter and Rotator Based on a Double-etched Directional Coupler," Optics Epress, vol. 22, No. 3, pp. 2489-2496, year 2014.
Bhandari et al., "Highly Efficient Broadband Silicon Nitride Polarization Beam Splitter Incorporating Serially Cascaded Asymmetric Directional Couplers," Optics Letters, vol. 45, No. 21, pp. 5974-5977, year 2020.
Guan et al., "Ultracompact Silicon-on-insulator Polarization Rotator for Polarization-diversified Circuits," Optics Letters, vol. 39, No. 16, pp. 4703-4706, year 2014.
Popov et al., "A Laser Speckle Pattern Technique for Designing an Optical Computer Mouse," Optics and Lasers in Engineering, vol. 42, pp. 21-26, year 2004.
Jo et al., "SpeDo: 6 DOF Ego-Motion Sensor Using Speckle Defocus Imaging," Columbia University, pp. 1-13, year 2015.
Gupta, "SpeDo: 6 DOF Ego-Motion Sensor Using Speckle Defocus Imaging," YouTube demonstration, pp. 1-2, year 2016, as downloaded from https://youtu.be/lilBMx4oKLM.
Amzajerdian et al., "Navigation Doppler Lidar for Autonomous Ground, Aerial, and Space Vehicles," NASA, pp. 1-2, year 2018.
Synopsys, Inc., "Designing Mode MUX/DEMUX Structures for Spatial Division Multiplexing Systems," pp. 1-7, year 2021, as downloaded from https://www.synopsys.com/photonic-solutions/product-applications/communications/beamprop-mode-sdm.html.
Pierrottet et al, "Navigation Doppler Lidar Sensor for Precision Altitude and Vector Velocity Measurements Flight Test Results,"

(56) References Cited

OTHER PUBLICATIONS

NASA, pp. 1-11, year 2011, as downloaded from https://ntrs.nasa.gov/api/citations/20120003317/downloads/20120003317.pdf.
Amazajerdian et al., "Doppler Lidar Sensor for Precision Landing on the Moon and Mars," NASA, pp. 1-7, year 2012, as downloaded from https://ntrs.nasa.gov/api/citations/20120003334/downloads/20120003334.pdf.
International Application # PCT/US2024/017201 Search Report dated May 13, 2024.
European search report, application EP 22 85 9075, dated Jul. 2, 2025.
Communication CF Form 1507, EP application # EP 22 859 075.8.
Communication CF Form 1507, EP application # 22 859 074.1.
Supplementary European search report, application # EP 22 85 9074, dated Jun. 26, 2025.
Communication CF Form 1507, EP application # EP 22 865 538.7.
Extended European search report, application # EP 22 86 5538, dated Jun. 12, 2025.
Supplementary European Search Report, Application No. EP 22 88 7986, dated Jul. 7, 2025.
International Application # PCT/US2024/038453 Search Report dated Oct. 18, 2024.
Extended European Search Report for European Application No. 23808482.6, dated Jul. 22, 2026, 13 Pages.
Figueiredo R.C., et al., "Semiconductor Optical Amplifier Space Switch With Symmetrical Thin-Film Resistive Current Injection," Journal of Lightwave Technology IEEE, USA, Jan. 15, 2017, vol. 35, No. 2, pp. 280-287, DOI: 10.1109/JLT.2016.2635202, ISSN: 0733-8724, XP011641221, [Retrieved On Feb. 13, 2017].
Office Action for Chinese Application No. 202280056392.6, mailed on Aug. 25, 2026, 7 pages.

* cited by examiner

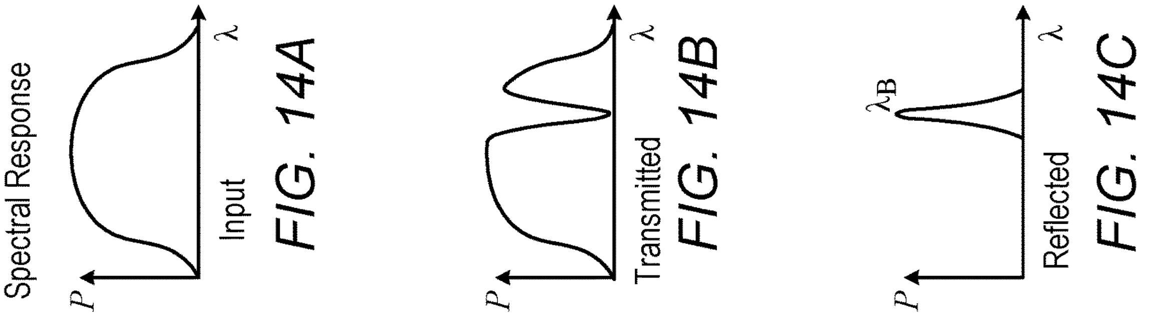
FIG. 14A
FIG. 14B
FIG. 14C
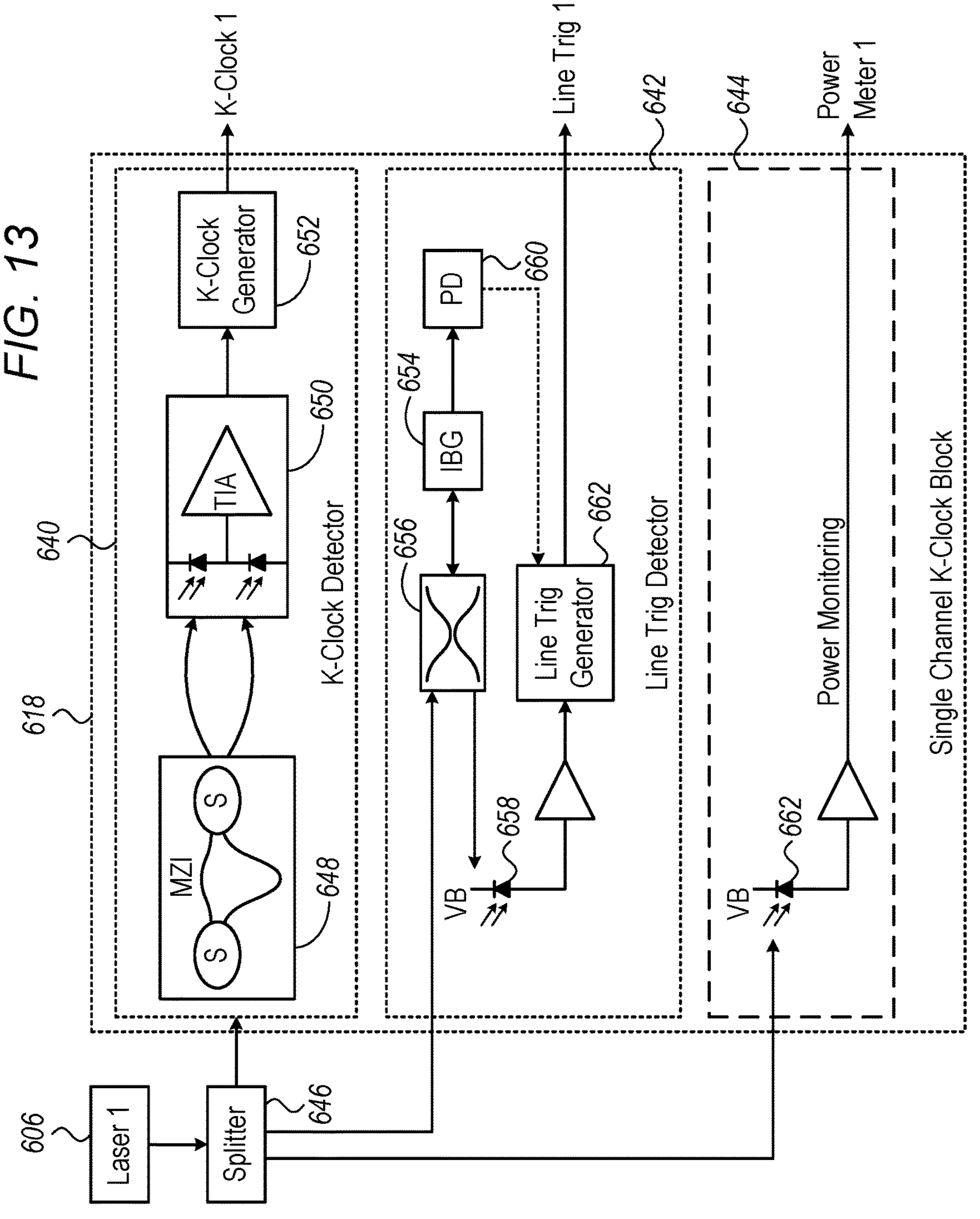
FIG. 13

INTEGRATED ARRAYS FOR COHERENT OPTICAL DETECTION

CROSS-REFERENCE TO RELATED APPLICATION

This application claims the benefit of U.S. Provisional Patent Application 63/234,700, filed Aug. 18, 2021; U.S. Provisional Patent Application 63/240,012, filed Sep. 2, 2021; and U.S. Provisional Patent Application 63/342,176, filed May 16, 2022. This application is related to another PCT patent application, filed on even date, entitled "Optical Transceiver Arrays". The disclosures of all these related applications are incorporated herein by reference.

FIELD OF THE INVENTION

The present invention relates generally to systems and methods for optical sensing, and particularly to integrated optical sensing devices.

BACKGROUND

In many optical sensing applications, multiple points on a target are irradiated by an optical beam or beams, and the reflected radiation from each point is processed to analyze properties of the target. In some applications, such as optical coherence tomography (OCT) and continuous-wave (CW) LiDAR, a coherent beam is transmitted toward the target, and the reflected radiation is sensed and processed coherently with the transmitted radiation. To sense the properties of the target with high resolution, the transmitted beam may be scanned over the target area, or an array of multiple beams may be transmitted and sensed simultaneously using an array of receivers.

The terms "optical," "light," and "optical radiation," as used in the present description and in the claims, refer to electromagnetic radiation in any of the visible, infrared, and ultraviolet spectral ranges.

SUMMARY

Embodiments of the present invention that are described hereinbelow provide improve systems, devices, and methods for optical sensing.

There is therefore provided, in accordance with an embodiment of the invention, an optoelectronic device, including a planar substrate and an array of optical transceiver cells disposed on the substrate. Each transceiver cell includes an optical transducer configured to couple optical radiation between the transceiver cell and a target external to the substrate. An optical distribution tree includes a network of waveguides and switches disposed on the substrate, coupled to convey coherent radiation from a radiation source to the optical transceiver cells. A controller is configured to actuate the switches so as to select different subsets of the optical transceiver cells that are to receive the coherent radiation from the optical distribution tree and to transmit the coherent radiation toward the target at different times during a scan of the target.

In some embodiments, the optical distribution tree includes multiple passive splitters, which divide the coherent radiation among the waveguides constituting branches of the tree. In one embodiment, the switches include semiconductor optical amplifiers (SOAs), which are coupled between one or more of the passive splitters and the waveguides constituting the branches of the tree, and the controller is configured to actuate and deactuated the SOAs in order to select the subsets of the optical transceiver cells that are to receive the coherent radiation from the optical distribution tree.

In some embodiments, the optical distribution tree includes multiple optical buses, wherein each optical bus is coupled to receive the coherent radiation from a respective one of the SOAs and to distribute the coherent radiation among a respective group of the optical transceiver cells. In a disclosed embodiment, each of the optical transceiver cells includes at least one tap coupled to extract a portion of the coherent radiation propagating through the optical bus for transmission of the coherent radiation via the optical transducer.

In some embodiments, each optical transceiver cell includes a receiver, which is coupled to mix a local part of the coherent radiation conveyed from the optical distribution tree to the optical transceiver cell with the optical radiation received by the optical transducer and to output an electrical signal responsively to the mixed radiation. In some of these embodiments, the optical distribution tree includes a first tree coupled to convey a first portion of the coherent radiation from the radiation source to the optical transceiver cells for transmission via the optical transducer toward the target, and a second tree coupled to convey a second portion of the coherent radiation from the radiation source to the optical transceiver cells to serve as the local part for mixing with the received optical radiation.

In a disclosed embodiment, the controller is configured to actuate the switches in both the first and second trees so that the optical transceiver cells in the selected subsets receive the coherent radiation simultaneously from both the first and second trees.

Additionally or alternatively, the second tree includes at least one optical delay line, configured to delay the second portion of the coherent radiation relative to the first portion. In a disclosed embodiment, the at least one delay line is configured to apply an adjustable delay to the second portion of the coherent radiation, and the controller is configured to set the adjustable delay responsively to a range of distances from the device to the target that is to be probed by the optical transceiver cells.

In one embodiment, the signal output by the receiver in each transceiver cell includes a beat frequency responsive to a range of the target from the device.

In some embodiments, the transceiver cells have respective fields of view, which are defined by respective optical apertures of the optical transducers, and the device includes a scanner, which is configured to scan the fields of view over the target. In a disclosed embodiment, as the scanner scans the fields of view over the target, the optical apertures define respective scan lines extending along a scan direction of the scanner, and the controller is configured to actuate the switches so as to select the scan lines to be probed by the device.

In another embodiment, the optical distribution tree includes at least first and second trees, which are coupled to convey the coherent radiation in at least first and second wavelength bands, respectively, to at least first and second sets of the optical transceiver cells simultaneously for coupling between the optical transceiver cells and the target.

There is also provide, in accordance with an embodiment of the invention, an optoelectronic device, including a planar substrate and an array of optical transceiver cells disposed on the substrate. Waveguides are disposed on the substrate and coupled to a source of coherent radiation, and are configured to define first and second optical networks, which are coupled to convey first and second portions, respectively, of the coherent radiation from the radiation source to the optical transceiver cells. At least one optical delay line is coupled to the second optical network and is configured to delay the second portion of the coherent radiation relative to the first portion.

In some embodiments, the at least one optical delay line includes a delay waveguide disposed on the substrate. Alternatively or additionally, the at least one optical delay line includes an optical fiber, which is coupled to the waveguides on the substrate.

In some embodiments, the at least one delay line is configured to apply an adjustable delay to the second portion of the coherent radiation. In one embodiment, the device includes a controller, which is configured to set the adjustable delay responsively to a range of distances from the device to a target that is to be probed by the optical transceiver cells. In a disclosed embodiment, the at least one delay line includes a plurality of delay lines having different, respective lengths, and an optical switch, which is configured to select at least one of the delay lines for coupling to the second optical network. In another embodiment, the at least one delay line includes a plurality of delay lines and an optical switch network, which is configured to selectively couple one or more of the delay lines together in series with the second optical network.

In one embodiment, the first and second optical networks respectively include multiple first and second subnetworks, which are coupled to convey the coherent radiation in multiple, respective wavelength bands, respectively, to at least first and second sets of the optical transceiver cells simultaneously, and the at least one optical delay line includes multiple optical delay lines which are coupled respectively to the second subnetworks.

There is additionally provided, in accordance with an embodiment of the invention, an optoelectronic device, including a planar substrate and an array of optical transceiver cells, including at least first and second disjoint sets of the optical transceiver cells, disposed on the substrate. Waveguides are disposed on the substrate and coupled to one or more sources of coherent radiation, including at least first coherent radiation in a first wavelength band and second coherent radiation in a second wavelength band, different from the first wavelength band, and are configured to define at least first and second optical networks, which are coupled to convey the first and second coherent radiation to the optical transceiver cells in the first and second sets, respectively.

In a disclosed embodiment, the at least first and second disjoint sets include at least three disjoint sets, and the waveguides are configured to define at least three optical networks, which are coupled to convey the coherent radiation in at least three wavelength bands over the at least three optical networks to the optical transceiver cells in the at least three sets, respectively.

In some embodiments, the transceiver cells have respective fields of view, and the device includes a scanner, which is configured to scan the fields of view over the target. In a disclosed embodiment, the first and second sets of the transceiver cells are arranged on the substrate so that as the scanner scans the fields of view, each area of the target is swept sequentially by at least a first transceiver cell in the first set and a second transceiver cell in the second set. Typically, the first and second sets of the transceiver cells are arranged in respective first and second columns of the array, extending along respective, parallel column axes, which are perpendicular to a direction of the scan.

In a disclosed embodiment, the device includes a plurality of lasers, which are configured to emit the coherent radiation in different, respective wavelength bands, including at least first and second lasers configured to emit the first and second coherent radiation, respectively. At least one interferometric optical circuit is configured to extract respective K-clocks from the coherent radiation emitted by the lasers in the respective wavelength bands. A controller is configured to process signals output by the optical transceiver cells in the different sets while synchronizing the signals based on the respective K-clocks.

There is further provided, in accordance with an embodiment of the invention, an optoelectronic device, including a plurality of lasers, which are configured to emit coherent radiation at respective wavelengths that are swept across different, respective wavelength bands. At least one calibration unit includes an interferometric optical circuit and is configured to extract respective K-clocks from the coherent radiation emitted by the lasers as the lasers are tuned across the respective wavelength bands. An array of optical transceiver cells are configured to direct the coherent radiation in the different wavelength bands toward a target and to output respective electrical signals responsively to optical radiation reflected from the target in each of the wavelength bands. A controller is configured to process signals output by the optical transceiver cells in the different sets while synchronizing the signals based on the respective K-clocks.

In one embodiment, the at least one calibration unit includes multiple channel calibration units, which are coupled to receive the coherent radiation from respective ones of the lasers and to extract respective channel K-clocks, and a global calibration unit, which is coupled to receive the coherent radiation from each of the lasers in succession and to extract respective global K-clocks, wherein the controller is configured to compute calibration factors for application to the signals by comparing the channel K-clocks to the global K-clocks.

In a disclosed embodiment, the at least one calibration unit includes line trigger detectors, which are configured to output signals as the wavelengths sweep through specified values. Additionally or alternatively, the at least one calibration unit includes a power monitor.

In one embodiment, the controller is configured to combine the synchronized signals to as to generate a depth map of the target.

There is moreover provided, in accordance with an embodiment of the invention, a method for sensing, which includes providing an array of optical transceiver cells disposed on a substrate. Each transceiver cell includes an optical transducer configured to couple optical radiation between the transceiver cell and a target external to the substrate. An optical distribution tree, including a network of waveguides and switches disposed on the substrate, is coupled to convey coherent radiation from a radiation source to the optical transceiver cells. The switches are actuated so as to select different subsets of the optical transceiver cells that are to receive the coherent radiation from the optical distribution tree and to transmit the coherent radiation toward the target at different times during a scan of the target.

There is furthermore provided, in accordance with an embodiment of the invention, a method for sensing, which includes providing an array of optical transceiver cells disposed on a substrate. Waveguides are arranged on the substrate to define first and second optical networks. The first and second optical networks are coupled to convey first and second portions, respectively, of coherent radiation from a source of coherent radiation to the optical transceiver cells. At least one optical delay line is coupled to the second optical network so as to delay the second portion of the coherent radiation relative to the first portion.

There is also provided, in accordance with an embodiment of the invention, a method for sensing, which includes providing an array of optical transceiver cells, including at least first and second disjoint sets of the optical transceiver cells, disposed on the substrate. Waveguides are arranged on the substrate to define at least first and second optical networks. The first and second optical networks are coupled to convey, respectively, at least first coherent radiation in a first wavelength band and second coherent radiation in a second wavelength band, different from the first wavelength band, from one or more coherent radiation sources to the optical transceiver cells in the first and second sets, respectively.

There is additionally provided, in accordance with an embodiment of the invention, a method for sensing, which includes operating a plurality of lasers to emit coherent radiation at respective wavelengths that are swept across different, respective wavelength bands. At least one calibration unit includes an interferometric optical circuit, to extract respective K-clocks from the coherent radiation emitted by the lasers as the lasers are tuned across the respective wavelength bands. An array of optical transceiver cells are coupled to direct the coherent radiation in the different wavelength bands toward a target and to output respective electrical signals responsively to optical radiation reflected from the target in each of the wavelength bands. Signals output by the optical transceiver cells in the different sets are processed while synchronizing the signals based on the respective K-clocks.

The present invention will be more fully understood from the following detailed description of the embodiments thereof, taken together with the drawings in which:

BRIEF DESCRIPTION OF THE DRAWINGS

FIG. 13 is a block diagram that schematically illustrates the operation of a calibration unit, in accordance with an embodiment of the invention;

FIGS. 14A, 14B, and 14C are spectral plots that schematically illustrate the operation of a calibration unit, in accordance with an embodiment of the invention;

DETAILED DESCRIPTION OF EMBODIMENTS

Overview

Figure 1:
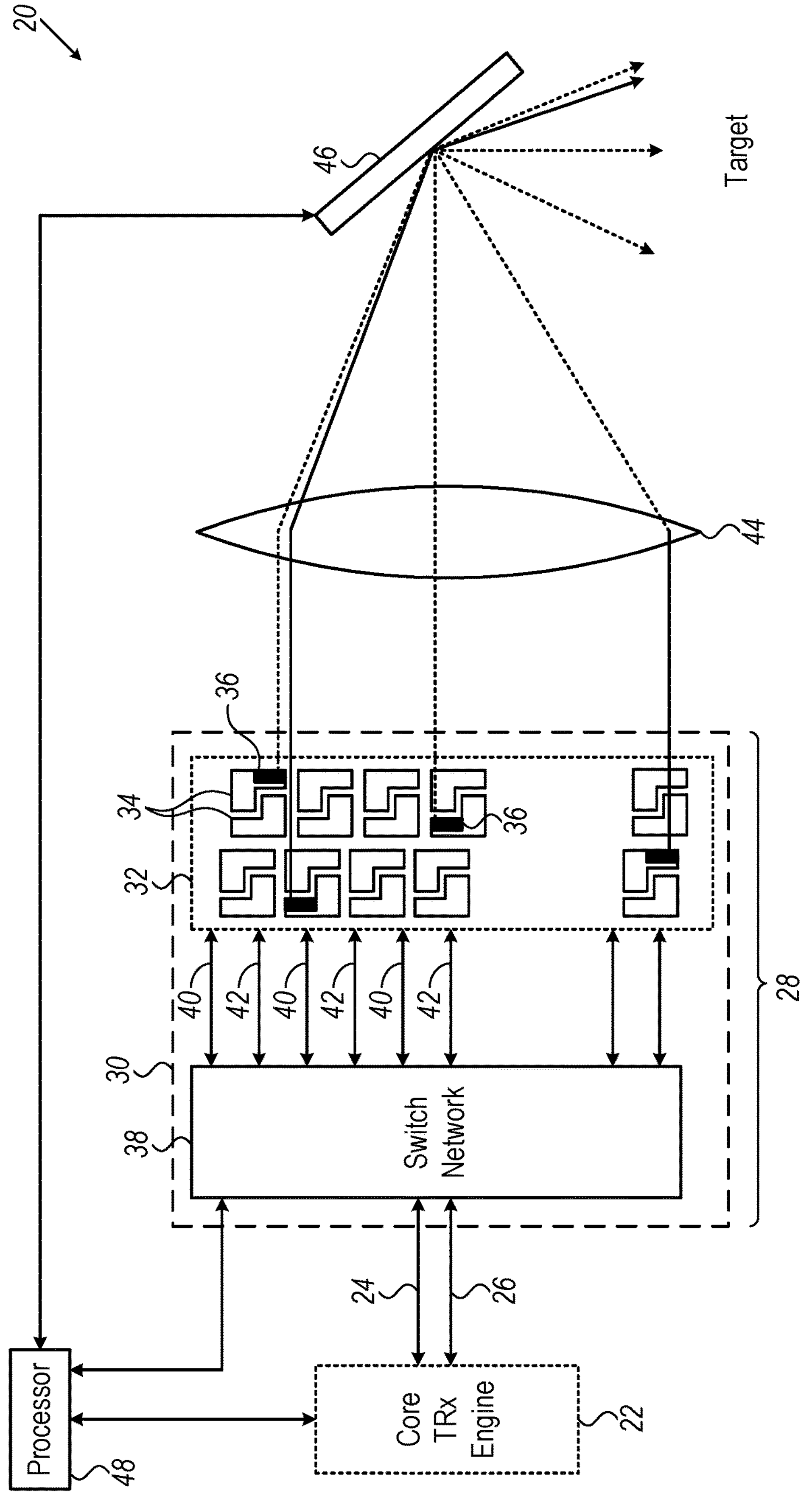
FIG. 1 is a block diagram that schematically illustrates an optical sensing system, in accordance with an embodiment of the invention.

As noted earlier, in coherent sensing applications, such as OCT and CW LiDAR, a coherent beam is transmitted toward a target, and the reflected radiation is sensed and processed coherently with the transmitted radiation. To sense the properties of the target with high resolution, the area of interest should be probed densely, either by scanning the transmitted beam over the area or by transmitting and sensing an array of multiple beams simultaneously. Scanning solutions, however, typically suffer from low throughput. Arrays of transmitters and receivers can improve throughput, but their resolution is limited by the pitches of the arrays, which are, in turn, limited by the sizes of the transmitters and receivers themselves.

Embodiments of the present invention address these problems by providing transceiver arrays and scanning systems that are able to scan a target with high resolution and high throughput. These embodiments use arrays of photonic sensing cells. In some embodiments, the arrays comprise transceiver cells, wherein each cell includes optical and optoelectronic components both for transmitting a beam of radiation and for receiving and detecting reflected radiation, along with ancillary electronics. In other embodiments, the cells may comprise components only for receiving and detection of radiation.

To reduce the size, power and complexity requirements of the sensing cells, the beams that are to be transmitted and/or mixed with the received radiation for coherent detection may be generated and modulated centrally, by a core transceiver engine, and then multiplexed among the sensing cells. A scanner, such as an optomechanical scanning device, scans the fields of view of all the cells over the area of interest so that the area is covered densely—with resolution finer than the physical pitch of the array of sensing cells—and with high throughput. The multiplexing and scanning may be controlled to tailor the scan area and resolution to application requirements. A variety of array geometries and scan patterns that can be used for these purposes are described below.

In the disclosed embodiments, the sensing cells themselves are typically produced using photonic integrated circuit (PIC) technology. These cells are designed to meet application requirements, such as the sensing mode and sensitivity, the mode of input/output coupling (for example, vertically or through the edge of the chip, via a grating or via a mirror), and wavelength characteristics (spectral range, and single—or multiple—wavelength sensing). A variety of representative embodiments are described below.

A number of applications of the present sensing cell arrays and scanning systems are described below by way of example. The principles of the present embodiments, however, may be readily extended and adapted to other applications involving multi-beam sensing. Furthermore, although the disclosed embodiments are directed to optical sensing, in the visible, infrared, or ultraviolet range, the principles of the present invention may alternatively be applied, mutatis mutandis, in other spectral ranges, such as microwave and millimeter-wave radiation. All such alternative applications are considered to be within the scope of the present invention.

Transceiver Arrays With Optical Switching

One of the challenges in producing compact coherent sensing arrays is to provide coherent optical radiation to all the cells of the array, with optical quality and power level sufficient to achieve high resolution and high signal/noise ratio (SNR). For some applications, such as continuous-wave (CW) LiDAR, the optical radiation should also be modulated. Incorporating an individual laser source in each cell increases the cell footprint and power dissipation substantially and may not achieve the desired optical quality.

It is therefore desirable to distribute the coherent radiation from a central, high-power source to the array of transceiver cells on the PIC substrate. For this purpose, some embodiments of the present invention provide optoelectronic devices that use an optical distribution tree, comprising a network of waveguides and switches disposed on the substrate, to convey coherent radiation from a radiation source to the optical transceiver cells. A controller actuates the switches so as to select different subsets of the optical transceiver cells to receive the coherent radiation from the optical distribution tree.

These selected transceiver cells transmit the coherent radiation toward the target, meaning that the optical power available for output from the device is concentrated in the desired subset of transceiver cells. The controller can select different subsets of the transceiver cells to actuate at different times during a scan, as well as setting parameters such as the output intensity and lengths of time during which the different subsets are actuated. Typically, a scanner scans the fields of view of the transceiver cells across the target, and the controller selects the parts of the target to scan and the corresponding scan parameters by jointly controlling the scanner and the optical distribution network.

The selected optical transceiver cells output electrical signals in response to the optical radiation that they receive from the target. These signals are amplified, sampled, digitized, and processed by processing circuits to generate depth and possibly velocity information with respect to the target. At least some of the processing circuits may be implemented together with the transceiver cells on the PIC; alternatively or additionally, processing circuits may be implemented on a separate electric IC. In either case, the controller may multiplex the processing circuits among the transceiver cells, so that the transceiver cells that are actuated at any given time are connected to the processing circuits, while non-actuated transceiver cells remain unconnected. This approach is helpful in reducing the number and size of the processing circuits and making optimal use of the available processing resources.

FIG. 1 is a block diagram that schematically illustrates an optical sensing system 20, in accordance with an embodiment of the invention.

In system 20, a core TRx engine 22 comprises one or more laser light sources, along with photonic and electronic circuit components for control, modulation, and distribution of the coherent radiation generated by the light sources. TRx engine 22 can implement a variety of different modulation schemes, such as amplitude modulation, frequency modulation and/or phase modulation, including chirped modulation for use in frequency-modulated continuous wave (FMCW) LIDAR and pseudo-random phase modulation for use in phase-modulated continuous wave (PMCW) LIDAR. The modulation may be applied by controlling the drive current supplied to the laser or lasers. Alternatively or additionally, TRx engine 22 may include features, such as a controllable gain medium or gratings, that can be used to modulate the outgoing light in response to electrical signals. Alternatively or additionally, the modulation may be applied externally, for example by optical modulation of the laser beam. TRx engine 22 is connected by one or more optical waveguides 24, and possibly also an electrical bus 26, to an optoelectronic sensing device 28, which is formed on a substrate 30.

In the embodiments described below, device 28 is fabricated using photonic integrated circuit (PIC) technology, and substrate 30 comprises a silicon die, for example in a silicon on insulator (SOI) configuration. Alternatively, substrate 30 may comprise other sorts of semiconductor or dielectric materials. Core TRx engine 22 may be disposed on substrate 30, as well, in which cases waveguides 24 and bus 26 may conveniently be formed on substrate 30, for example by photolithographic processes. Alternatively, core TRx engine 22 may be coupled to substrate 30 via one or more edge couplers or one or more grating couplers (not shown). Further alternatively, waveguides 24 and bus 26 may comprise optical fibers and conductive wires, respectively.

Device 28 comprises an array 32 of sensing cells 34 formed on substrate 30. Each sensing cell 34 comprises an optical transducer 36, which couples light in and out of the cell, along with photonic and electronic components, as shown in detail in the figures that follow. Sensing cells 34 may all be of the same type, or alternatively, device 28 may include two or more different types of sensing cells. In some embodiments, sensing cells 34 comprise transceiver (TRx) cells, including photonic components for both transmission and reception of light; and in this case, transducers 36 both transmit light toward a target and receive light reflected from the target. Alternatively or additionally, sensing cells 34 may comprise only receiving components, which receive light reflected from a target following transmission of the light through other channels (not shown).

Sensing cells 34 have respective fields of view, which are defined by the respective optical apertures of optical transducers 36 and by focusing optics 44, which project the optical apertures onto a target. A scanner 46 scans the fields of view over the target. (Although scanner 46 is shown in FIG. 1, for the sake of simplicity, to be scanning only in a direction parallel to the longitudinal axis of array 32, scanner 46 typically scans in a perpendicular direction or in two directions.) Each transducer 36 emits (and receives) a cone of light that is collimated by optics 44, and the resulting beam from each transducer is projected into a different angle in the field of view. In addition, scanner 46 can scan the beams to control the density of coverage of the field of view of system 20, including varying the density of coverage in different areas of the field. In this manner, even when the fields of view of transducers themselves cover the target only sparsely, the density of coverage will be filled in as desired over the entire target of areas of interest within the target.

In the pictured embodiments, scanner 46 comprises one or more rotating mirrors, which scan over the target along one or two scan axes. Alternatively or additionally, the scanner may comprise a motion assembly, which shifts optics 44 in a transverse direction, or any other suitable type of mechanical, optical, or wavelength-based scanner, for example. Generally speaking, scanner 46 may operate by mechanical scanning (for example using a galvanometer mirror, or MEMS mirrors with one or two scanning directions); movement of a lens and/or sensor (for example using a piezoelectric actuator, VCM, or thermal scanner); wavelength scanning in combination with a dispersive element, such as a prism or grating; polarization-based scanning; phased array scanning; modulation of a liquid lens or mirror; liquid crystal on silicon (LCOS) scanning; digital micromirror devices; or any other suitable mechanism that is known in the art.

A switch network 38 on substrate 30 distributes light received through waveguides 24 among multiple optical buses 40, which comprise waveguides coupled to deliver the light to different, respective sets of sensing cells 34. Switch network 38 also couples electrical signals between electrical bus 26 and electrical buses 42, for transfer of the electrical signals to and from sensing cells 34. Switch network 38 also comprises an optical distribution tree, which may comprise an active optical network, comprising optoelectronic components which select the buses 40 to which the light is to be distributed. Alternatively or additionally, switch network 38 may comprise a passive optical splitter array.

The use of active optical switching adds complexity to device 28 but enables the optical energy provided through waveguides 24 to be distributed selectively among sensing cells 34. This sort of active, switched network can be used to select individual sensing cells or groups of sensing cells to be activated in scanning over a target. As scanner 46 scans the fields of view of sensing cells 34 over the target, the optical apertures of optical transducers 36 define respective scan lines extending along the scan direction of the scanner, and a controller (such as a processor 48) can actuate the switches in switch network 38 so as to select the scan lines to be probed by device 28. In this manner, for example, certain rows of a raster scan can be selected for sensing in different areas of the target; and the spacing between raster rows can be varied depending on the desired resolution. Thus, the available optical energy can be concentrated in the sensing cells in locations corresponding to regions of interest in the target.

To summarize, the scheme shown generally in FIG. 1 enables a flexible choice of scanning characteristics and scan pattern by appropriate choices of the geometrical layout of array 32, scanning of the fields of view of sensing cells 34 by optics 44 and/or scanner 46, and switch network 38. The operation of system 20 can thus be controlled in both the spatial and temporal dimensions to enrich the information content of the projected and received images. A given spatial location can thus receive information from several different modalities, multiplexed by temporal scanning. In addition, scanning in any one dimension effectively projects points along the other dimension along the temporal axis, and thus opens up possibilities of spatio-temporal multiplexing with enriched collection of information as a result. Furthermore, the interplay between fast switching (optical and/or electrical) by switch network 38 and the scanning modalities described above creates additional scanning possibilities, such as varying the dwell time on the target dynamically as needed, as well as adaptive control of resolution and frame rate and configurable definition of regions of interest.

Processor 48 controls the operation of system 20 and receives signals output by sensing cells 34 in response to light received by device 28. Processor 48 typically comprises a general-purpose microprocessor, with suitable analog and digital interfaces for controlling and receiving signals from the components of system 20. Alternatively or additionally, processor 48 may comprise special-purpose digital logic and other hardware components, which may be hard-wired or programmable. Processor 48 processes the signals output by sensing cells 34 in order to reconstruct features of the target. For example, processor 48 may generate a depth map of the target using techniques of optical coherence tomograph (OCT) for short-range targets or CW LIDAR for longer-range targets.

In some embodiments, processor 48 actuates sensing cells 34 selectively, i.e., the processor receives signals from different sensing cells in different sweeps of scanner 46 or even during a single sweep. As noted earlier, when switch network 38 comprises an active optical network, it can be controlled in this context to direct the light from core TRx engine 22 to the sensing cells that are active at any given instant and thus use the available optical power more efficiently. By selective activation of sensing cells 34, processor 48 can vary the resolution of a scan and/or concentrate sensing resources in a certain region of interest of the target. Additionally or alternatively, processor 48 can control parameters including the range and speed of scanner 46, the intensity of the beams transmitted toward target, and the integration time of sensing cells 34 in order to adjust the range, resolution, and SNR of any given scan. Details of this functionality are described further hereinbelow with reference to the figures that follow.

Figure 2:
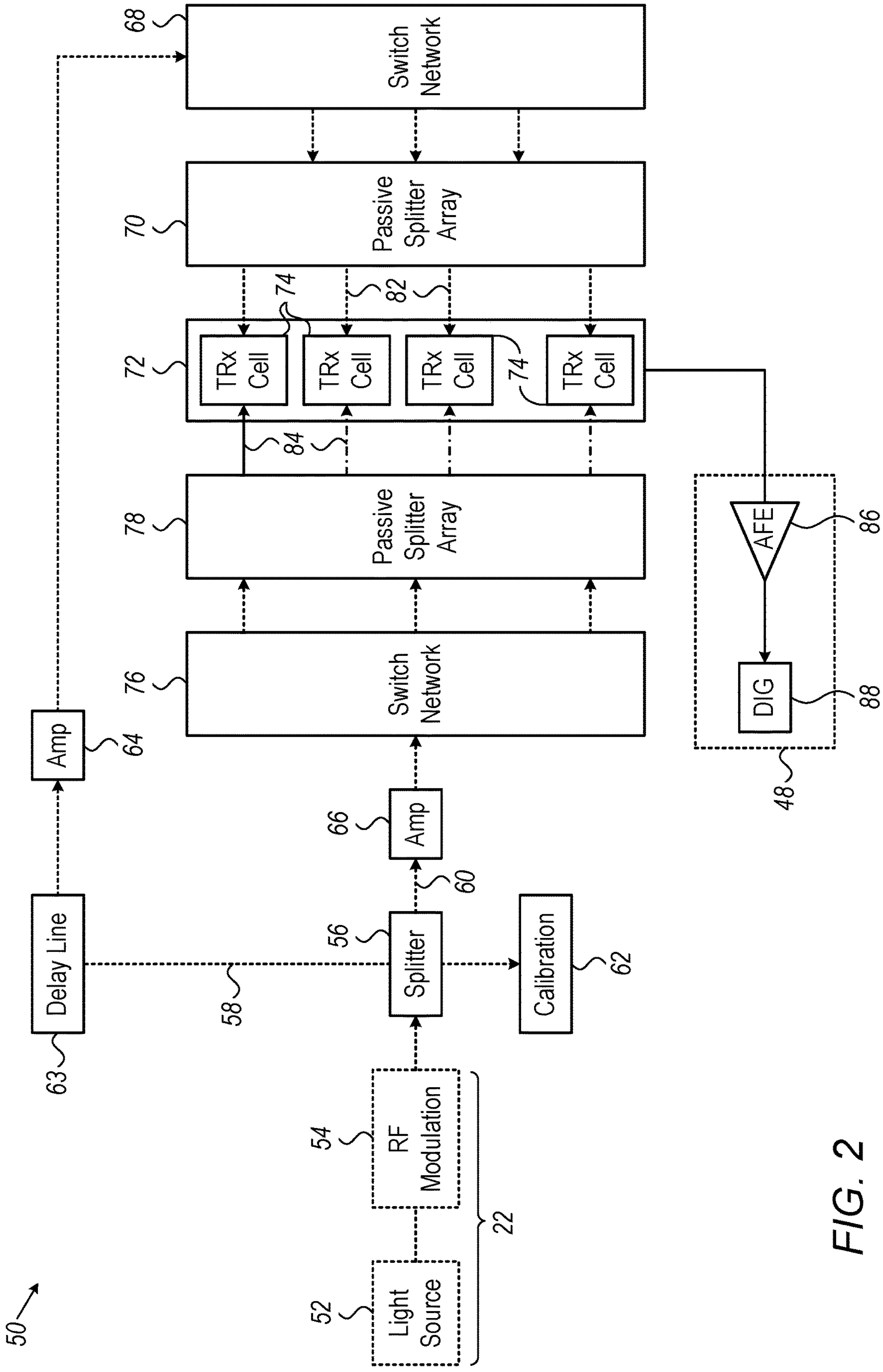
FIG. 2 is a block diagram that schematically shows details of an optical sensing system, in accordance with an embodiment of the invention.

FIG. 2 is a block diagram that schematically shows details of an optical sensing system 50, in accordance with an embodiment of the invention. System 50 is similar in its construction and principles of operation to system 20 and is described here to illustrate particular implementation features. Elements of system 50 with functionality similar to that of corresponding elements of system 20 are labeled with the same indicator numbers.

Optical radiation emitted by a light source 52 is modulated by an RF modulator 54, for example to apply a frequency chirp for purposes of frequency-modulated CW (FMCW) LIDAR. A splitter 56 splits the modulated beam between a reference arm 58, a signal arm 60, and a calibration unit 62. The beams in reference arm 58 and/or signal arm 60 may be amplified by optical amplifiers 64, 66, such as semiconductor optical amplifiers (SOAs). The beam in reference arm 58 is routed by a switch network 68 to a subset of the passive splitters in a passive splitter array 70, and is then fed as a local oscillator (LO) beam via optical buses 82 to a subset of TRx cells 74 in an array 72.

The beam in signal arm 60 is routed by a switch network 76, through a passive splitter array 78 via optical buses 84, typically (although not necessarily) to the same subset of TRx cells 74 as the LO beam. Switch networks 70 and 76 operate together, under the control of processor 48, to select and activate the desired subsets of TRx cells 74. The selected TRx cells 74 transmit the beams provided by buses 84 toward the target and then receive radiation reflected from the target and mix the received radiation with the LO beams provided by buses 82. Alternatively, TRx cells may receive both the transmitted and LO beams from the same optical bus.

The resulting electrical signals are amplified and filtered by an analog front end (AFE) 86 and then input to a digital processing block 88. Digital processing block 88 includes, for example, an analog/digital converter (ADC), which converts the analog signals to digital sample; a digital signal processor (DSP), which processes the signals to extract data, such as depth and velocity information; and a controller, such as processor 48 (FIG. 1), which orchestrates system operation and may include switching controls, scanning controls, and laser controls, for example. In FMCW sensing, for example, digital processing block 88 extracts the beat frequencies of the signals output by the selected TRx cells 74 and thus measures the ranges and velocities of points on the target. To reduce the cost and power consumption of system 50 the processing resources of AFE 86 and/or digital processing block 88 may also be multiplexed among TRx cells 74.

Calibration unit 62 extracts a phase-synchronized clock signal from the modulated beam that it receives from splitter 62. Calibration unit 62 may also monitor transmission parameters, such as modulation, coherence, power, etc. Features of this calibration unit are described further hereinbelow.

Figure 3:
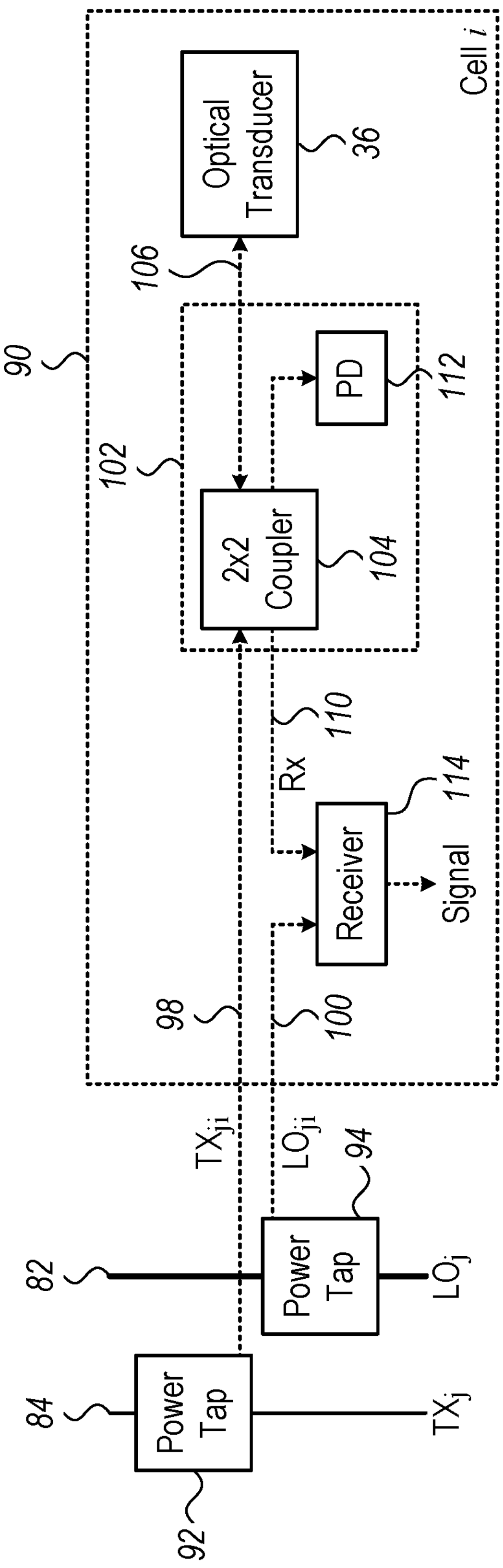
FIG. 3 is a block diagram that schematically shows details of an optical transceiver cell, in accordance with an embodiment of the invention.

FIG. 3 is a block diagram that schematically shows details of optical transceiver cell 90, in accordance with an embodiment of the invention. Transceiver cell 90 may be used in place of sensing cells 34 in FIG. 1 or TRx cells 74 in FIG. 2. Alternatively, other transceiver cell designs, such as those shown in FIGS. 3, 6-9, and 11 of the above-mentioned PCT patent application, entitled "Optical Transceiver Arrays." may be used in the devices and systems described herein.

Cell 90 comprises a pair of taps 92 and 94, which extract respective portions of the coherent radiation propagating in buses 84 and 82 for input to a transmit waveguide 98 and a LO waveguide 100, respectively. Alternatively, both transmit waveguide 98 and LO waveguide 100 may receive the Tx and LO beams, respectively, from the same optical bus; or cell 90 may comprise a single tap to bus 84, with an internal splitter (not shown) to split off a small part of the Tx beam to serve as the LO beam. A photonic circuit 102 in cell 90 comprises a coupler 104, which passes the outgoing coherent radiation via a waveguide 106 to optical transducer 36 for transmission toward the target. Transducer 36 may comprise a grating coupler or edge coupler, for example, such as the types of transducers shown in FIGS. 13-19 and 5A-C of the above-mentioned PCT patent application.

Figure 4:
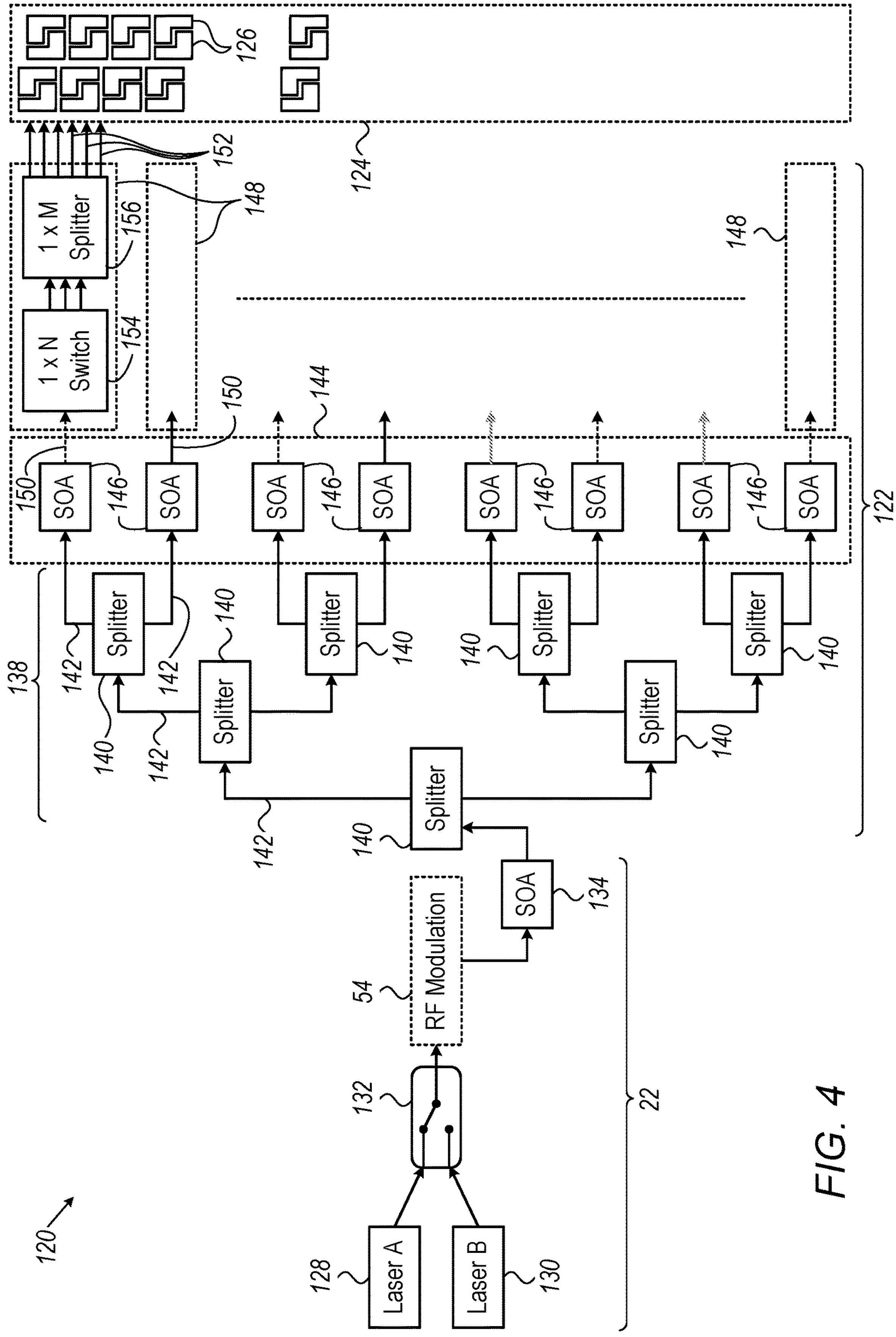
FIG. 4 is a block diagram that schematically shows details of an optical sensing system, in accordance with another embodiment of the invention.

Transducer 36 also receives incoming radiation from the target and conveys the incoming radiation via waveguide 106 and coupler 104 to a receive waveguide 110. Transducer 36 may comprise a PBSR (not shown), to enable cell 90 to receive and process incoming radiation of both polarizations. A receiver 114 mixes the coherent radiation from LO waveguide 100 with the incoming radiation received via coupler 104 through receive waveguide 110 and generates a corresponding electrical output signal. Receiver 114 typically comprises a mixer, such as a 2×2 optical coupler, or a pair of mixers in an optical hybrid, along with a suitable detector or detectors, such as a balanced pair of photodiodes (not shown in the figures), for example as shown in FIGS. 4 and 5 of the above-mentioned PCT patent application. Assuming the coherent beams carried by buses 82 and 84 to be suitably modulated, for example with a frequency chirp, the electrical output signal will comprise a beat frequency indicative of the range and velocity of the target.

Coupler 104 may comprise a directional coupler or a beamsplitting coupler, such as a polarization beamsplitter rotator (PBSR). A photodiode 112 may be attached to a beamplitting coupler for termination and monitoring. The beamsplitting coupler may be a balanced 50/50 coupler, or it may alternatively be unbalanced, for example an 80/20 coupler, which conveys only 20% of the energy in the Tx beam toward transducer 36, while conveying 80% of the incoming radiation to receive waveguide 110. This sort of configuration is useful in applications in which there are limits (such as safety limits) on the optical power projected toward the target.

FIG. 4 is a block diagram that schematically shows details of an optical sensing system 120, in accordance with another embodiment of the invention. System 120 is similar in its construction and principles of operation to the systems described above and is described here particularly to illustrate features of an optical distribution tree 122. Elements of system 120 with functionality similar to that of corresponding elements of system 20 (FIG. 1) are labeled with the same indicator numbers. Although FIG. 4 shows only the single optical distribution tree 122, which carries both the transmitted and LO light to an array 124 of transceiver cells 126, the principles of this embodiment may likewise be implemented in systems using separate distribution trees for the transmitted and LO light, such as system 50 (FIG. 2). Alternatively, the optical distribution tree may convey only the transmitted light to the transceiver cells, while the transceiver cells generate the LO light locally.

TRx engine 22 in system 120 comprises a pair of lasers 128, 130, with an optical switch 132 to select one of the two lasers as input. This arrangement can be used for redundancy in case one of the lasers malfunctions, to enhance system reliability, or to switch between two different wavelengths, thus providing a multispectral functionality. In another embodiment, lasers 128 and 130 have slightly different wavelength, to enable switching in case of interference with another system. Alternatively, switch 132 can be configured as a 2×2 element, feeding two separate optical distribution trees. Further alternatively, switch 132 can be configured to select among a larger number of lasers, or system 120 can operate with only a single laser, as in the preceding embodiments.

Further alternatively, optical switch 132 may be replaced by a switch matrix (not shown, which routes the beams from multiple lasers to different sub-trees within optical distribution tree 122. This switch matrix can route lasers that are in good operational condition to their respective sub-trees dynamically, and thus enable multispectral imaging, for example, with built-in redundancy.

In one embodiment, lasers 128 and 130 comprise CW lasers. The beam selected by switch 132 is modulated in phase and/or frequency by radiofrequency (RF) modulator 54, with a modulation bandwidth of 1-10 GHz, for example. Modulator 54 may implement an optical I/Q scheme, for example, using a Mach Zehnder interferometer on the PIC.

This modulation scheme is typically lossy, and the modulated beam is therefore amplified by a semiconductor optical amplifier (SOA) 134. In another embodiment, lasers 128 and 130 are modulated directly, for example by controlling the electric current drive, in which case external RF modulator 54 is not required and can be omitted.

Figure 8:
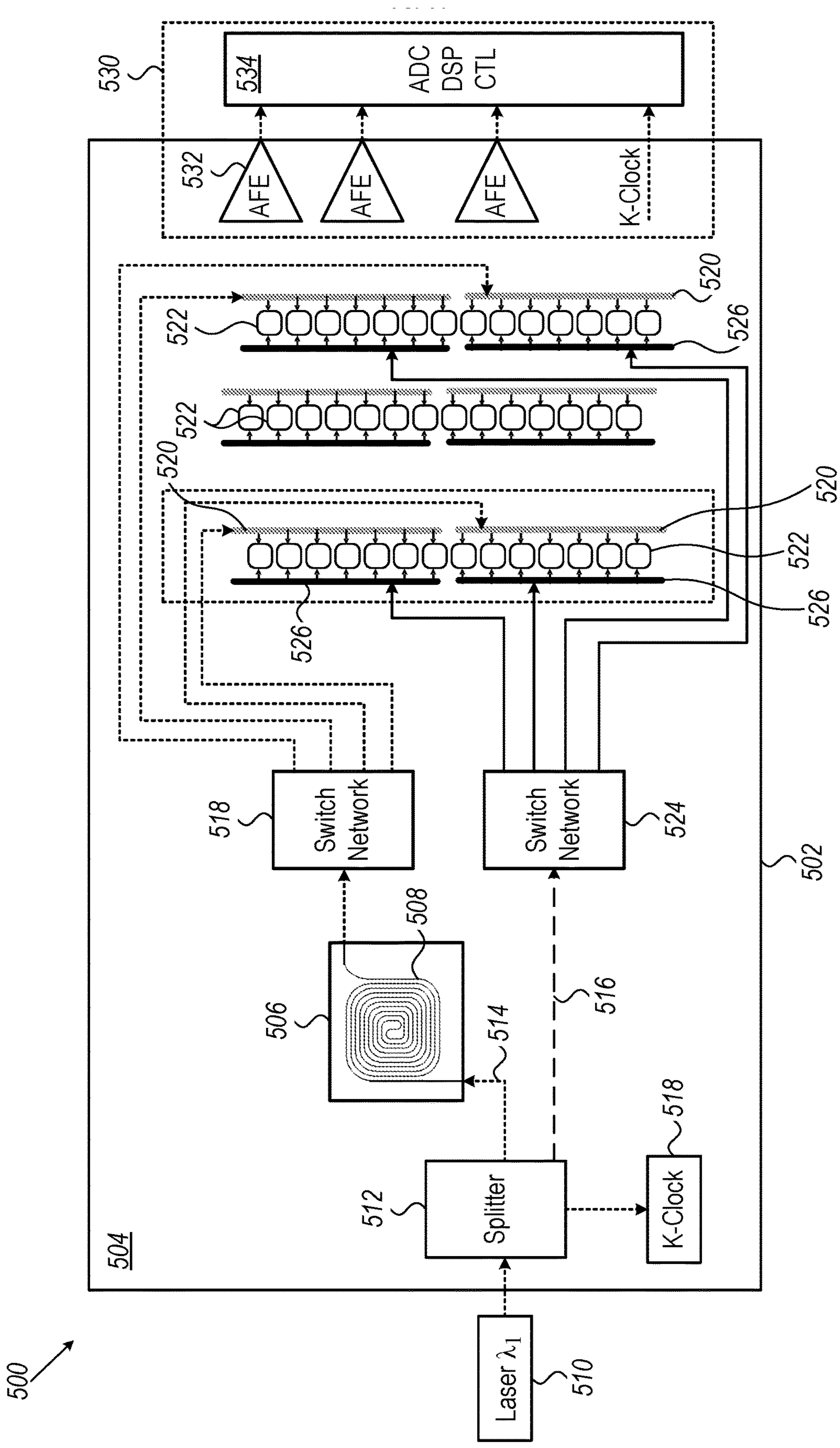
FIG. 8 is a block diagram that schematically illustrates an optical sensing system, in accordance with another embodiment of the invention.

Optical distribution tree 122 comprises a passive stage 138, in which multiple passive splitters 140 divide the coherent radiation output by TRx engine 22 among waveguides 142, constituting the branches of the tree. Passive stage 138 feeds an active stage 144, in which SOAs 146 serve as optical switches. Each SOA 146 is coupled between a respective passive splitter 140 and a waveguide 150 serving a switching sub-network 148 of tree 122. Processor 48 (FIG. 1) actuates and deactuates SOAs 146 in order to select the subsets of optical transceiver cells 126 that are to receive the coherent radiation from the optical distribution tree. Optical distribution tree 122 feeds multiple optical buses 152, each of which is coupled via sub-network 148 to receive coherent radiation from a respective SOA 146 and to distribute the coherent radiation among a respective group of one or more of optical transceiver cells 126. In an alternative embodiment (as shown in FIG. 8, for example) each SOA 146 serves a single optical bus 152 for distribution of the coherent radiation to the respective group of transceiver cells.

In the present embodiment, following amplification by SOA 146, light is further routed in the corresponding sub-network 148 by a 1×N switch matrix 154 and further split by an array of 1×M splitters 156. In this example, therefore, sub-network 148 can select 0, M, 2M, . . . , K*M transceiver cells 126 to be activated simultaneously. When the corresponding SOA 146 is off, the unamplified signal will be dissipated by switch matrix 154 and splitters 156. Alternatively, one or several ports of the switch matrix can be chosen to be used as a drain or for monitoring. The inactive transceiver cells can also be disabled electronically, so that any optical signal transmitted or returned by the inactive transceiver cells will not be interpreted or recorded.

One practical benefit of the SOA-based switching scheme in optical distribution tree 122 is that the optical signals are routed on the PIC and brought close to transceiver cells 126 at low optical power. Sub-networks 148 may have only a small footprint. Because the amplification in SOAs 146 occurs close to the optical transducers, losses associated with routing high-power optical signals across the PIC are minimized.

The order of passive stage 138, active stage 144, switch matrixes 154, and splitters 156 in optical distribution tree 122 is shown in FIG. 4 by way of example, and these elements may alternatively be arranged in different orders and configurations. Additionally or alternatively, some of the elements can be removed or duplicated. All such alternative configurations are considered to be within the scope of the present invention.

For example, the PIC may be partitioned at waveguides 150 into a source PIC, which includes the SOAs, and a main PIC. The source PIC may be coupled to the main PIC, for example, by edge couplers to the main PIC (starting with waveguides 150). This partitioning and other modes of partitioning are also considered to be within the scope of the present invention.

Figure 5A:
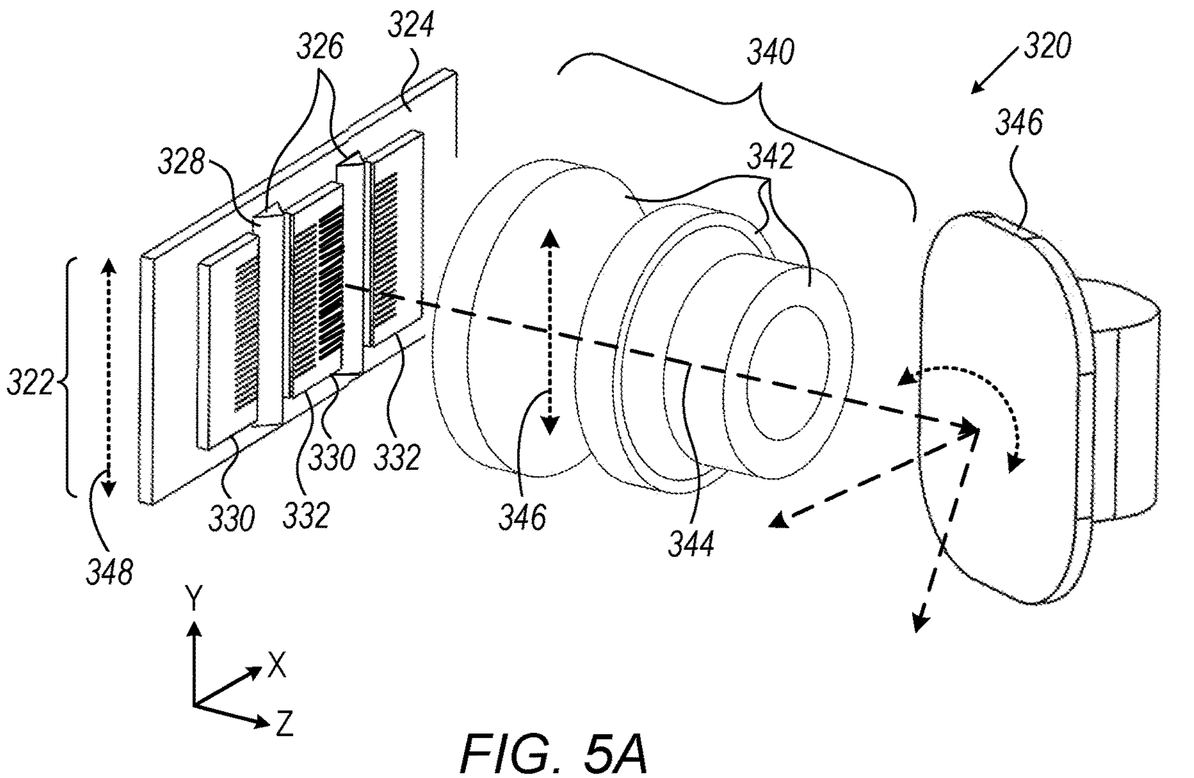
FIG. 5A is a schematic pictorial view of an optical sensing system, in accordance with an embodiment of the invention.
Figure 5B:
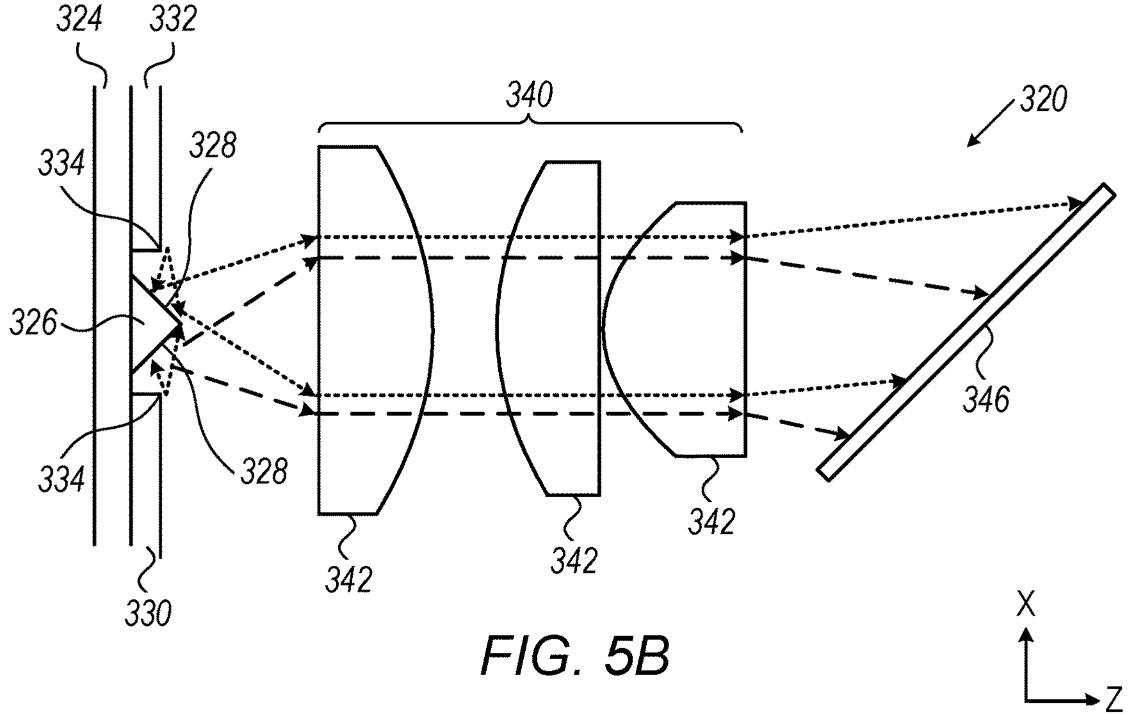
FIG. 5B is a schematic sectional view of the optical sensing system of FIG. 5A.
Figure 5C:
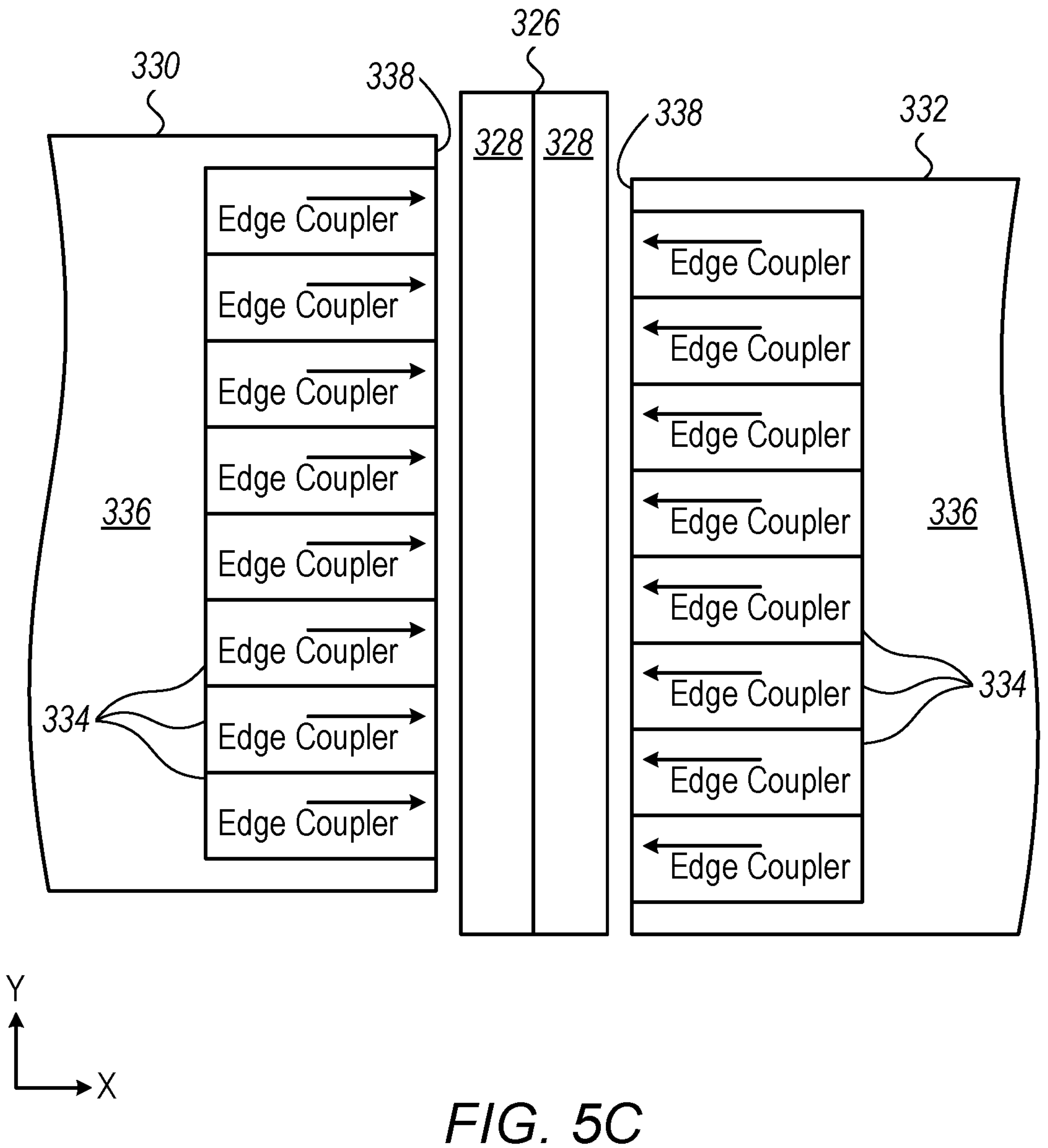
FIG. 5C is a schematic frontal view showing details of a coupling arrangement used in the optical sensing system of FIG. 5A, in accordance with an embodiment of the invention.

Reference is now made to FIGS. 5A, 5B and 5C, which schematically illustrate an optical sensing system 320, in accordance with an embodiment of the invention. FIG. 5A is a pictorial view of optical sensing system 320, while FIG. 5B is a sectional view of the optical sensing system. FIG. 5C is a schematic frontal view showing details of a coupling arrangement used in optical sensing system 320.

System 320 comprises a sensing subassembly 322, comprising a carrier substrate 324, with one or more dual folding mirrors 326 mounted on the carrier substrate. Dual folding mirror 326 comprises a pair of reflecting surfaces 328 disposed at opposite angles relative to a normal to carrier substrate 324. In the pictured embodiments, dual folding mirror 326 has a triangular profile, with reflecting surfaces 328 oriented respectively at +45° and −45° relative to the normal, which is parallel to the Z-axis in the coordinate system shown in the figure. Alternatively, other sorts of folding mirrors may be used. Although subassembly 322 is shown in FIG. 5A to comprise two dual folding mirrors 326 with associated sensing devices 330, 332, in alternative embodiments, the sensing subassembly may comprise only a single dual folding mirror and associated sensing devices; or it may comprise three or more dual folding mirrors and sensing devices.

Sensing subassembly 322 comprises a pair of sensing devices 330 and 332 mounted on carrier substrate 324 on opposing sides of dual folding mirror 326. Each sensing device 330, 332 comprises a planar device substrate 336, which is mounted on carrier substrate 324 such that an edge of device substrate 336 is in proximity to a corresponding reflecting surface 328 of dual folding mirror 326. Each sensing device 330, 332 comprises a respective array of transceiver cells formed on the corresponding device substrate 336, along with an optical switching network, for example as illustrated in the preceding figures and described above.

The transceiver cells in devices 330 and 332 comprise optical transducers in the form of respective edge couplers 334, which are arrayed along an edge 338 of device substrate 336 so as to couple optical radiation between the cells and the proximate reflecting surface 328. Edges 338 are both parallel to the Y-axis, as is the longitudinal axis of dual folding mirror 326. Edge couplers 334 have a certain pitch, i.e., the center-to-center distance between adjacent edge couplers along the Y-axis, which is limited by the constraints of the PIC technology that is used to produce devices 330 and 332. To increase the scan density, edge couplers 334 can be staggered, i.e., edge couplers 334 in device 332 can be offset along the Y-axis by half the pitch relative to edge couplers 334 in device 330, as shown in FIG. 5C. A scan pattern that takes advantage of this staggering is illustrated in FIG. 7A-D.

Edge couplers 334 define the respective optical apertures of the transceiver cells in the arrays on devices 330 and 332. Imaging optics 340, comprising one or more optical elements 342, image these optical apertures along an optical axis 344 onto the target, thus defining the respective field of view of each transceiver cell. A scanner scans the fields of view of the sensing elements across the target. In the embodiment shown in FIG. 5A, the scanner comprises a rotating mirror 346, which is disposed between dual folding mirror 326 and the target and scans the imaged optical apertures across the target. Rotating mirror 346 may comprise, for example, a single- or dual-axis galvanometer or MEMS (microelectromechanical systems) mirror assembly or a rotating polygonal mirror. Alternatively, other sorts of scanners, such as Risley prisms, may be used.

Additionally or alternatively, the scanner in system 320 may operate by shifting at least one of optical elements 342 and/or shifting carrier substrate 324 in a direction transverse to optical axis 344. The shift of one of optical elements 342 is represented in FIG. 5A by an arrow 346, while the shift of carrier substrate 324 is represented by an arrow 348. Both shifts are parallel to the Y-axis in the pictured embodiment, and will accordingly shift the fields of view of the transceiver cells in the Y-direction, while rotating mirror 346 scans the fields of view of the transceiver cells along the X-axis.

In some embodiments of the present invention, processor 48 (FIG. 1) controls the optical switching network and other capabilities of the transceiver device scanning a target selectively, to identify and extract detailed information with respect to regions of interest. For example, to make optimal use of the available sensing and processing resources, the fields of view of the transceiver cells may first be scanned across a target area at a certain (typically coarse) resolution, and the signals output by the transceiver cells are processed to identify a region of interest within the target area. For example, processor 48 may identify shapes and ranges of objects in this first scan and select a region or regions contain objects of interest.

After identifying a region of interest in this manner, the fields of view of the transceiver cells are scanned selectively across the region of interest, typically with a resolution finer than the resolution of the first scan. The signals output by the transceiver cells during the high-resolution scan are processed in order to produce a high-quality three-dimensional (3D) map of the region of interest. Specific techniques for selecting and scanning the region of interest and enhancing the quality of 3D mapping in the region are described in greater detail in the above-mentioned PCT patent application entitled "Optical Transceiver Arrays," for example in reference to FIG. 34.

Figure 6:
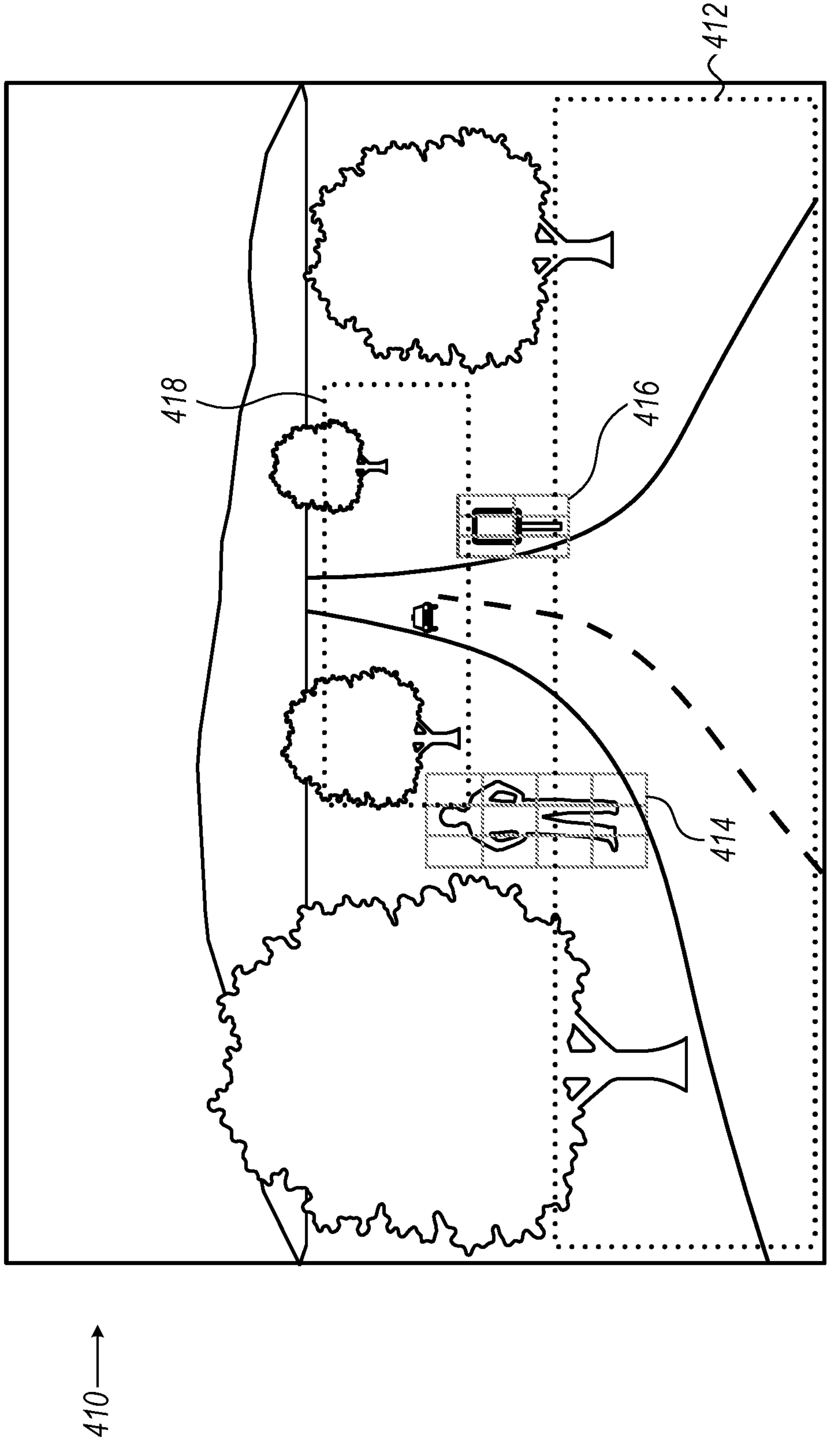
FIG. 6 is a schematic frontal view of a scene that is scanned by an optical sensing system, in accordance with an embodiment of the invention.
Figure 7A:
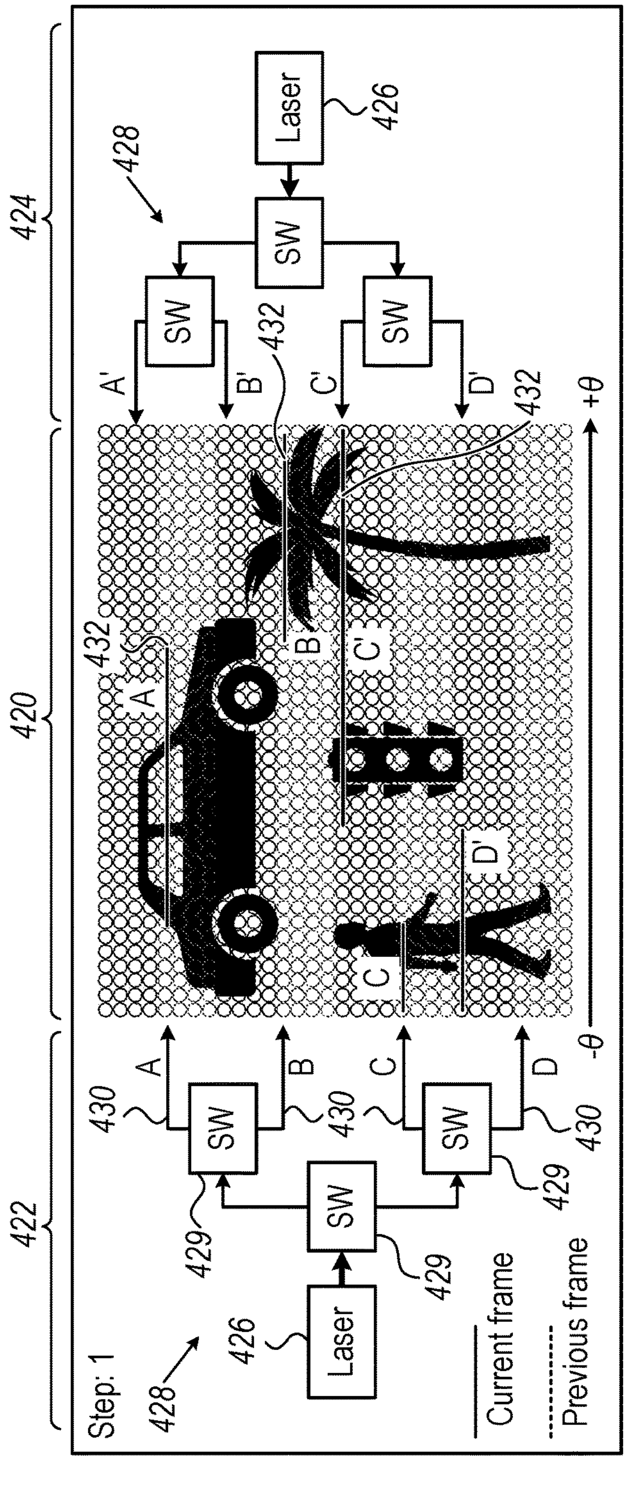
FIGS. 7A, 7B, 7C and 7D are schematic frontal views of successive scan patterns applied across a scene by a switched optical sensing system, in accordance with an embodiment of the invention.
Figure 7B:
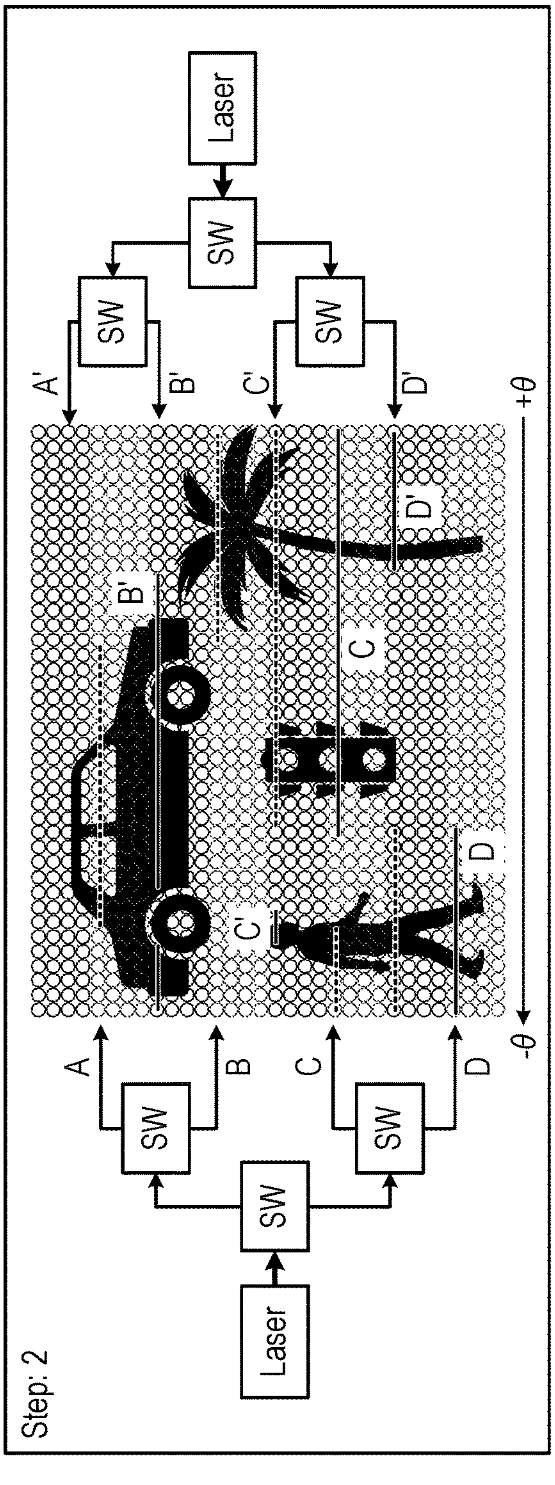
Figure 7C:
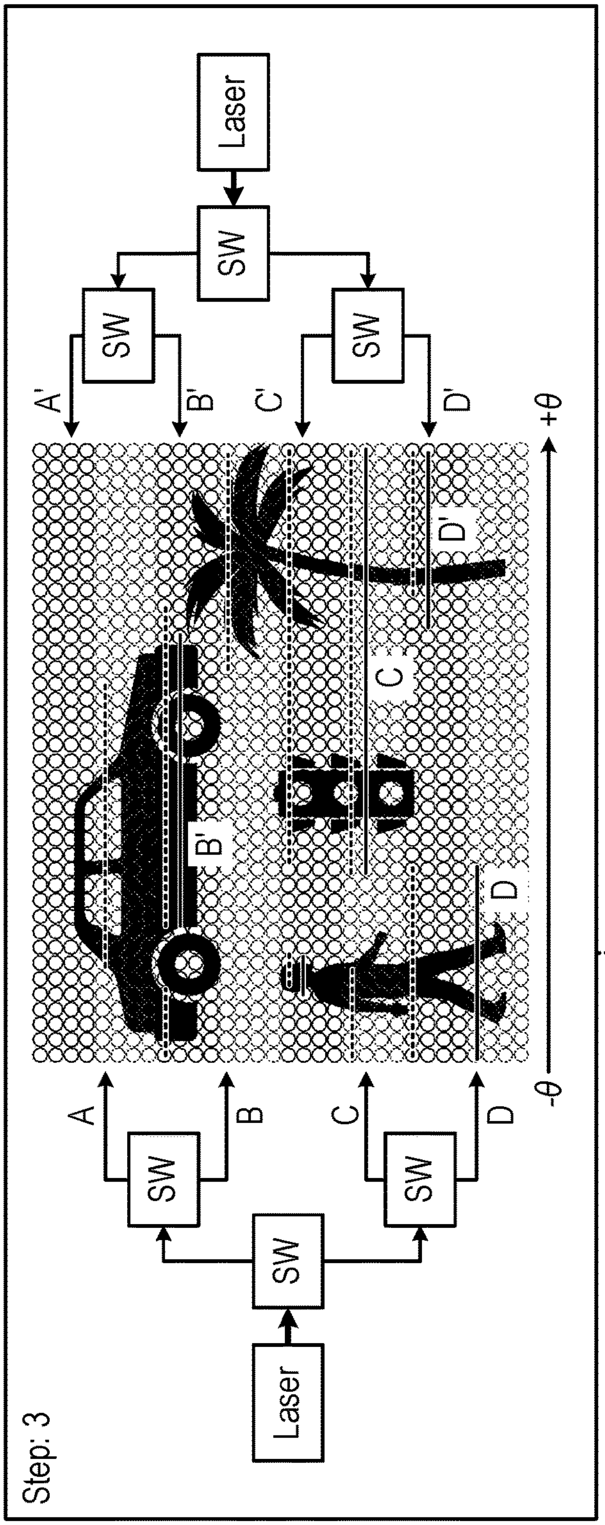
Figure 7D:
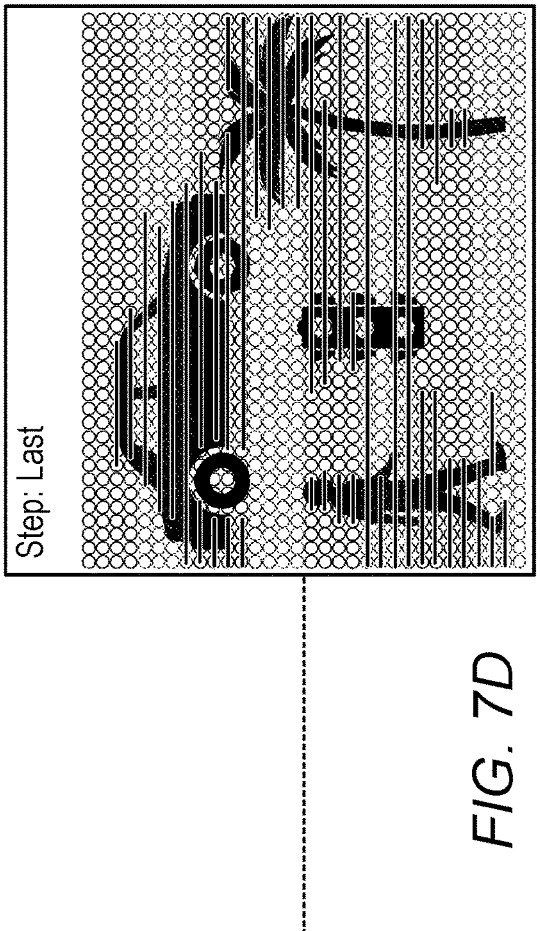

FIG. 6 is a schematic frontal view of a scene 410 that is scanned by an optical sensing system, such as the systems shown in the preceding figures, in accordance with an embodiment of the invention. The sensing system initially scans scene 410 with coarse resolution and thus identifies regions and features of interest in the scene. In the present example, these regions include:

- A short-range region 412. In the absence of objects of interest within this region, processor 48 will subsequently set a low scan resolution for this region.
- Regions of interest 414, 416. Processor 48 recognizes that these mid-range regions contain objects of possible significance. Therefore, processor 48 will set a high scan resolution and low scan speed for these regions.
- A long-range region of interest 418. Processor 48 recognizes that this region contains objects of importance, including the road and other vehicles, at large distances from the sensing system. Therefore, processor 48 assigns a reduced scan speed and increased transmitted radiation intensity for scanning this region.

FIGS. 7A, 7B, 7C and 7D are schematic frontal views of successive scan patterns applied across a scene 420 by a switched optical sensing system, in accordance with an embodiment of the invention. In the present example, the sensing system includes two sensing devices 422 and 424 with staggered scan lines, which may be similar to sensing devices 330 and 332 as shown in FIGS. 5A-C. For simplicity of illustration, each sensing device 422, 424 includes a respective laser source 426 and an optical switching network 428, which distributes the laser radiation to transceiver cells 430. When particular transceiver cells 430 are actuated by switching network 428, they give rise to respective scan lines 432, which are labeled A-D and A'-D', respectively.

FIGS. 7A-D illustrate the use of preferential switching and application of optical power in the areas of interest in scene 420, i.e., areas that are considered to contain information of value, while reducing resource use in less interesting areas. In this example, optical switching networks 428 in devices 422 and 424 comprises switches 429, which switch quickly between transceiver cells 430 and thus actuate different scan lines, for example switching between lines A and B, between lines C and D, between lines A' and B', and between lines C' and D'. A galvanometer mirror, such as mirror 346 (FIG. 5A) scans alternately from left to right (as in "step 1," FIG. 7A) and then from right to left (in "step 2," FIG. 7B). After each pair of galvanometer scans, the scan lines are shifted vertically, for example by piezoelectric actuation of the optics or sensing devices (as described above), thus shifting the scan lines vertically by a small increment, for example by a single pixel in the output depth map.

Thus, in the frames marked step 1, step 2, and step 3 (FIGS. 7A, 7B and 7C), different switches 429 in optical switching networks 428 are actuated for different parts of each of the scans. Switches 429 are toggled in the middle of each scan line 432 in order to turn the corresponding transceiver cells on as the scan crosses a region of interest and off elsewhere. At the conclusion of the process (in "step last," FIG. 7D), each of the regions of interest has been covered by scan lines.

Transceiver Arrays With Optical Delay Lines

Some coherent sensing applications, such as OCT, use laser sources with short coherence lengths. In these applications, it is desirable that the LO beam delivered to each of the transceiver cells be delayed, so that the effective optical path length of the LO beam is roughly equal to the actual optical path length of the radiation that is transmitted to and reflected back from the target to the transceiver cells. In the embodiments that are described below, an optical delay line is incorporated in the path of the LO beam in order to delay the LO beam relative to the transmitted beam.

FIG. 8 is a block diagram that schematically illustrates an optical sensing system 500, in accordance with an embodiment of the invention. System 500 comprises a coherent optical sensing device 502, implemented on a PIC 504. Device 502 is similar in its construction and principles of operation to the systems described above, but with the addition of an optical delay line 506 in the LO beam path. Although optical delay line 506 is implemented in FIG. 8 in the form of a waveguide 508 on PIC 504, in alternative embodiments the delay line may comprise a suitable optical fiber and/or other optical components.

A light source 510 outputs coherent optical radiation. Depending on application requirements, the radiation may be modulated, and it may have a fixed wavelength or wavelength band (typically a broad band for OCT), or the wavelength may be scanned. A splitter 512 splits the modulated beam between a reference arm 514, a signal arm 516, and a calibration unit 518. In applications that use wavelength scanning, calibration unit 518 may extract a phase-synchronized K-clock from the scanned beam in order to synchronize the measurements made by device 502 in the frequency domain, as described further hereinbelow.

The beam in reference arm 514 is routed through an optical distribution tree that includes delay line 506 and an optical switch network 518 to multiple LO optical buses 520. Each LO bus 520 serves a respective group of optical transceiver cells 522. When a given LO bus 520 is selected by optical switch network 528, it provides the LO beam to the respective group of transceiver cells. As noted above, this LO beam is delayed by delay line 506 relative to the transmitted beam in signal arm 516.

The beam in signal arm 516 is routed by an optical switch network 524 to multiple transmit optical buses 526, typically (although not necessarily) to the same subset of transceiver cells 522 as the LO beam. Switch networks 518 and 524 operate together, under the control of processor 48 (FIG. 1), to select and activate the desired subsets of transceiver cells 522. The selected transceiver cells 522 transmit the beams provided by buses 526 toward the target and then receive radiation reflected from the target and mix the received radiation with the LO beams provided by buses 520. By selective activation of different transceiver cells at different times, system 500 is able to cover a large area of the target with high throughput while avoiding interference that might otherwise arise between neighboring transceiver cells.

As in the preceding embodiments (for example as shown in FIG. 3), transceiver cells 522 each comprise an optical transducer, which couples the portion of the coherent radiation delivered by bus 526 toward a target external to the substrate and receives optical radiation reflected from the target. Typically, a scanner (as shown in FIG. 1 or 5A, for example), scans the fields of view of transceiver cells 522 over the target. A receiver in each transceiver cell 522 mixes the optical radiation received by the optical transducer with the portion of the coherent radiation delivered by bus 520 and outputs an electrical signal responsively to the mixed radiation. The electrical signal output by the receiver in each of the transceiver cells is indicative of the range of the target from device 502.

As in the embodiment of FIG. 2, the electrical signals output by transceiver cells 522 are conveyed to an electronic processing unit 530, which includes an analog front end (AFE) 532 and a digital processing block 534. Digital processing block 534 typically includes an ADC and a DSP, which processes the signals to extract data, such as depth information, along with a controller, such as processor 48. To reduce the cost and power consumption of system 500 the processing resources of AFE 532 and/or digital processing block 534 may also be multiplexed among the transceiver cells. In frequency-scanned operation, the phase-synchronized K-clock extracted by calibration unit 518 is applied in digital processing block 534 to ensure that the samples are uniformly separated in frequency space.

Because of the short coherence length used in sensing applications such as OCT, the optimal delay of the LO beam can vary depending on the distance to the target. Thus, in some embodiments, as shown in the figures that follow, an optical delay line within the optical distribution tree is configured to apply an adjustable delay to the LO beam. A controller, such as processor 48, is able to set the adjustable delay depending on the range of distances from the device to the target that is to be probed by the optical transceiver cells. The adjustable optical delay lines that are shown in the figures that follow may be implemented either as waveguides on a PIC chip or using off-chip elements, such as fiberoptics or free-space optics.

Figure 9:
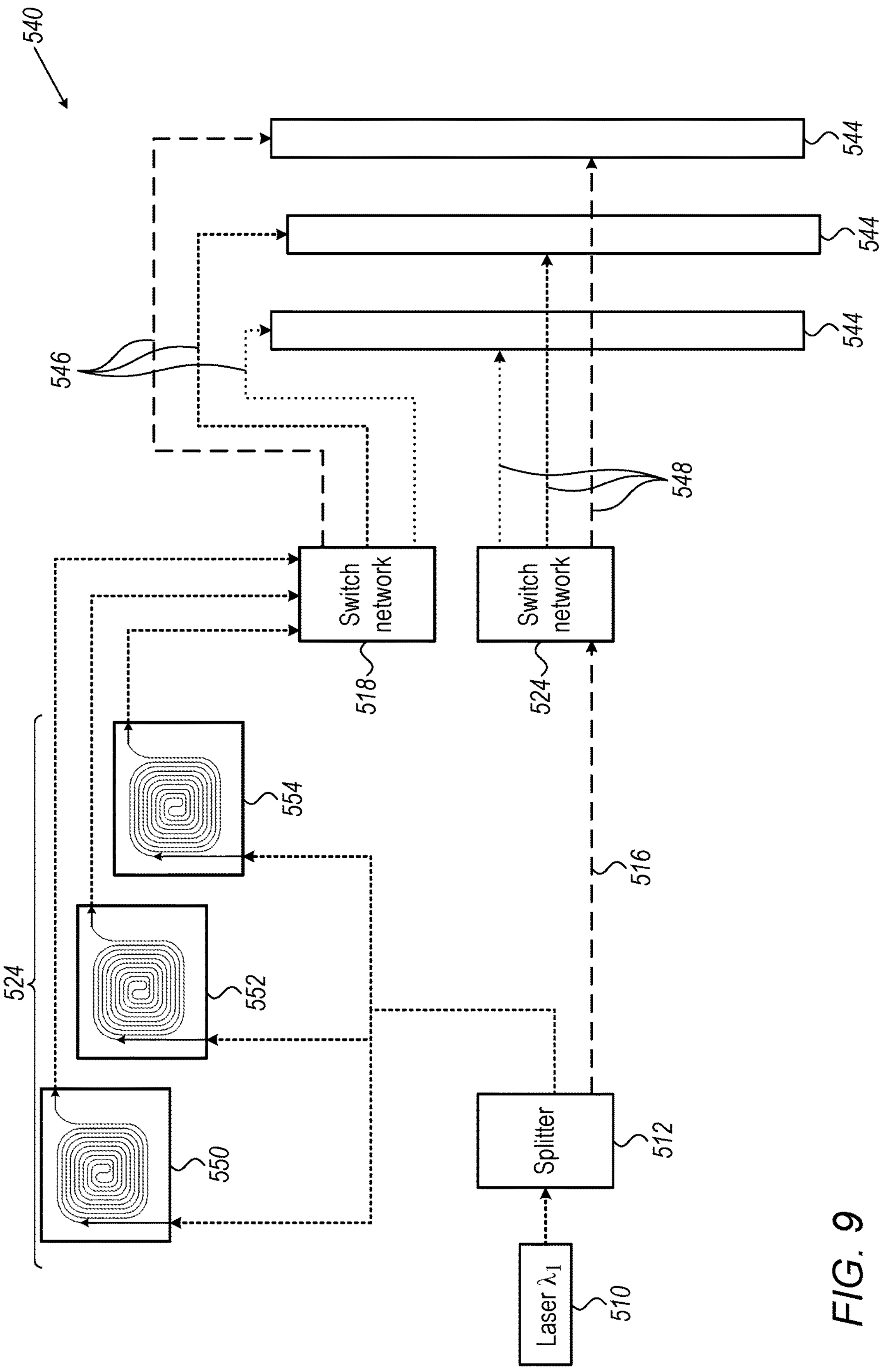
FIG. 9 is a block diagram that schematically illustrates an optical sensing system, in accordance with yet another embodiment of the invention.

FIG. 9 is a block diagram that schematically illustrates an optical sensing system 540, in accordance with another embodiment of the invention. System 540 is similar to system 500 (FIG. 8), and similar components are referred to by the same indicator numbers in FIG. 9 as were used in FIG. 8.

As in the preceding embodiment, light source 510 outputs coherent optical radiation. Splitter 512 splits the modulated beam between reference arm 514 and signal arm 516. The beam in reference arm 514 is routed through an optical distribution tree that includes an adjustable delay line 542 and optical switch network 518 via LO buses 546 to selected groups 544 of transceiver cells. The beam in signal arm 516 is similarly routed by optical switch network 524 via signal buses 548 to groups 544 of the transceiver cells. Optical switch network 518 may include SOA-based switching, as described above, as well as other types of switches, such as thermos-optic switches.

Adjustable delay line 542 comprises multiple delay lines 550, 552, 554, having different, respective lengths. (Although FIG. 9 shows three delay lines 550, 552 and 554 of different lengths, adjustable delay line 542 may alternatively comprise a smaller or larger number of different delay lines.) One or more optical switches in network 518 select at least one of delay lines 550, 552 and 554 for coupling through the network to buses 546. Various coupling configurations are possible. For example, in one embodiment the same delay line 550, 552 or 554 is coupled to all the groups 544 of transceiver cells, so that all the transceiver cells sense the same depth range. Alternatively, different delay lines may be coupled respectively to different groups of transceiver cells, so that each group senses a different depth range. In yet another embodiment, each bus 546 comprises multiple sub-buses, each carrying an LO beam with a different, respective delay, and the transceiver cells may comprise taps and an optical switch (not shown) to select the desired LO beam.

Figure 10:
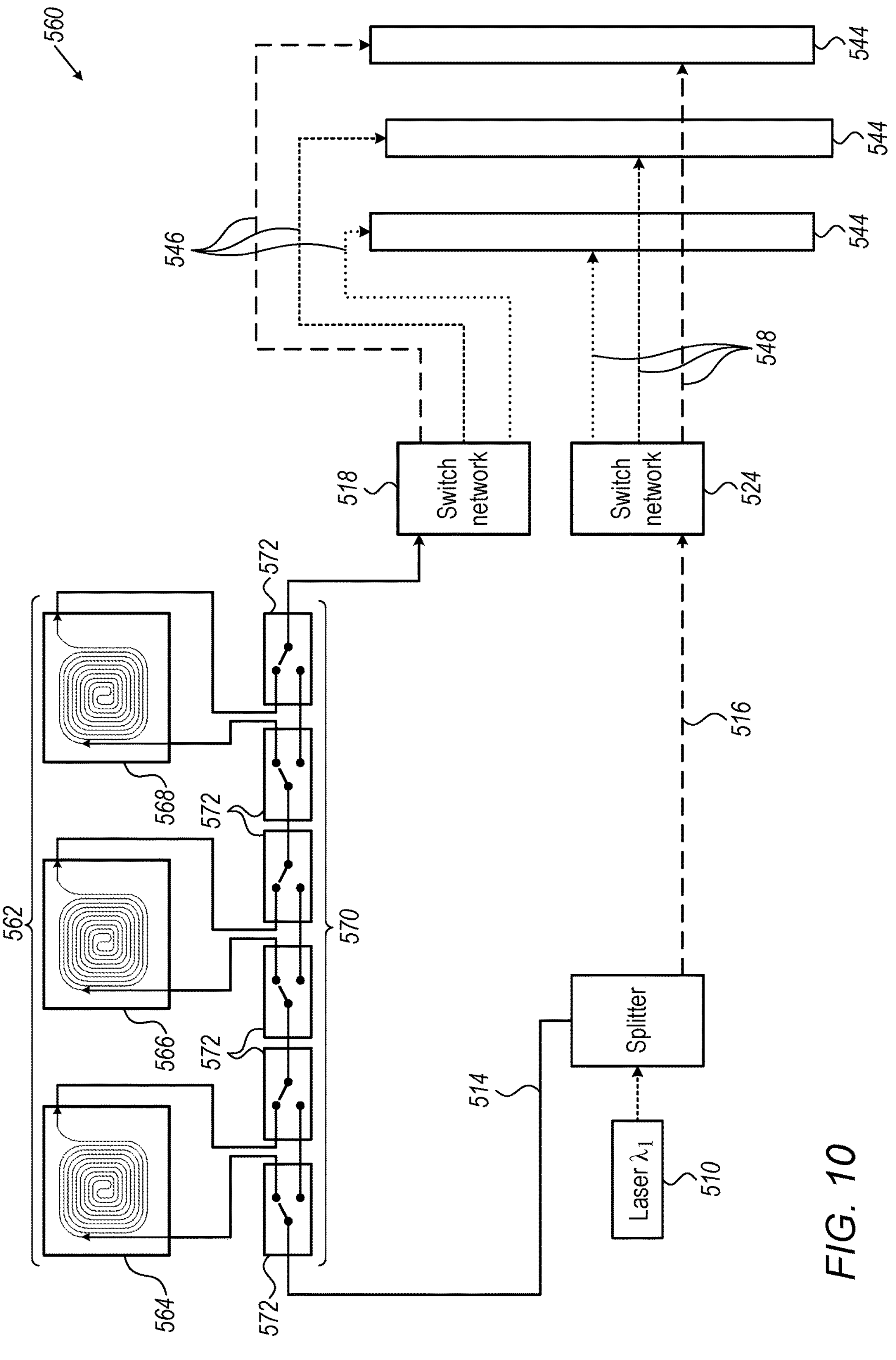
FIG. 10 is a block diagram that schematically illustrates an optical sensing system, in accordance with a further embodiment of the invention.

FIG. 10 is a block diagram that schematically illustrates an optical sensing system 560, in accordance with another embodiment of the invention. System 560 is similar to system 540 (FIG. 9), except for the configuration of an adjustable delay line 562 in system 560. Therefore, the description of FIG. 10 will be limited to the features of the adjustable delay line.

In system 560, adjustable delay line 562 comprises multiple delay lines 564, 566, 568, which may have the same or different, respective lengths. An optical switch network 570 comprises multiple switches 572, which can be configured to selectively couple one or more of delay lines 564, 566, 568 together in series with optical switch network 518, for delivery to buses 546. (Although FIG. 10 shows three delay lines 564, 566 and 568, adjustable delay line 562 may alternatively comprise a smaller or larger number of delay lines.) Switch network 570 can be controlled to apply and set the delay applied to the LO beam during each scan, or even to adjust the delay dynamically during a scan. Although adjustable delay line 562 in FIG. 10 has only a single output to switch network 518, the adjustable delay line may alternatively have multiple output taps, taken from different points in switch network 570, so that LO beams with different delays may be output to different groups 544 of transceiver cells.

Figure 11:
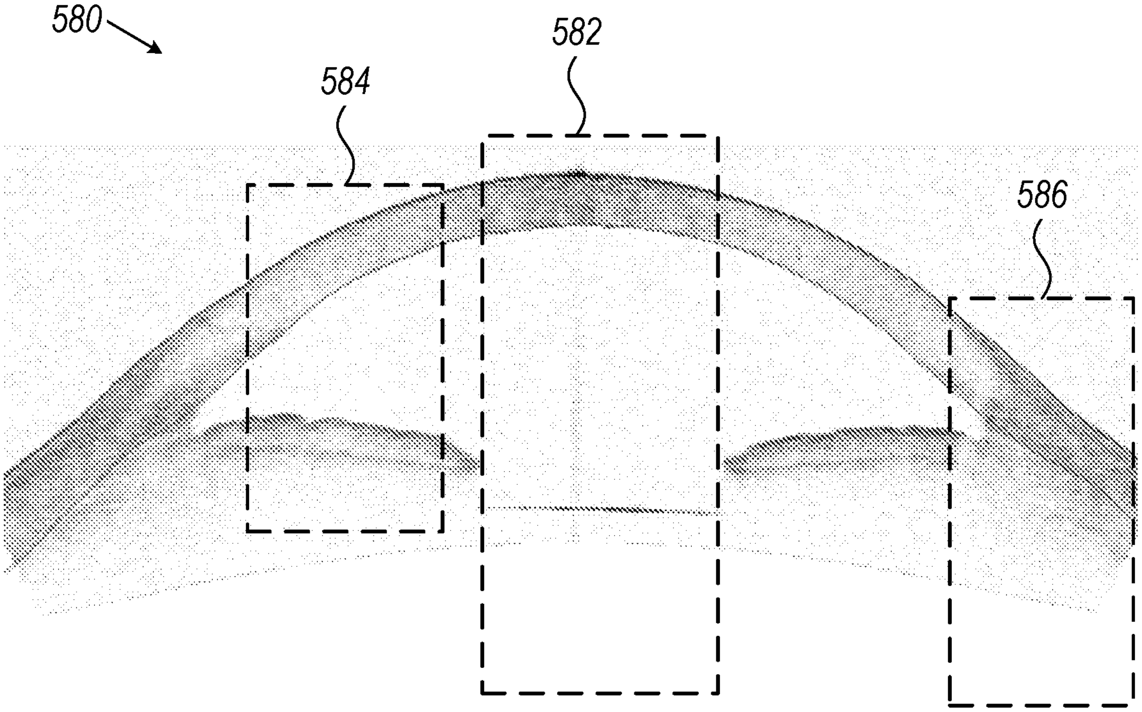
FIG. 11 is a schematic sectional representation of an eye as seen in an OCT scan carried out using a coherent optical sensing system in accordance with an embodiment of the invention.

In one embodiment, adjustable delay line 562 can be used to create a sort of photonic digital/analog converter (DAC). For the purpose, the lengths of delay lines 564, 566 and 568 are chosen to be L, 2L and 4L, and additional delay lines (not shown) can be added to the chain with lengths of 2^ (k−1)*L. For each delay line, the corresponding optical switches 572 determine whether the LO beam will go through the delay line or bypasses it, going straight on the next delay line. By controlling switches 572, the controller can create any delay between 0 and (2^ k−1)*L, in units of L. FIG. 11 is a schematic sectional representation of an eye 580 as seen in an OCT scan carried out using a coherent optical sensing system with an adjustable delay line in the LO optical network, in accordance with an embodiment of the invention. This sort of scan may be carried out, for example, using system 540 or 560 (FIG. 9 or 10).

In this example, a processor defines three different windows 582, 584, 586 within a scan across eye 580, and sets a different delay setting for each window to accommodate for the different depths of the anatomical structures in the eye relative to the optical sensing device. The delay settings may be chosen on the basis of an initial scan over the eye or, alternatively, based on a priori knowledge of the anatomy. Thus, in a central window 582, two different delay values may be used to accommodate the large depth range covering the cornea and pupil. In peripheral windows 584 and 586, different delay settings are used to provide high-resolution views of the iris and limbal area. The processor stitches the windows together to generate an image of the entire eye 580, with enhanced resolution in areas of interest.

Although the embodiments described above relate specifically to delaying the LO beam in a coherent sensing device, the principles of these embodiments may alternatively be applied in other applications in which multiple optical networks, comprising waveguides on a substrate, distribute respective portions of coherent radiation from a radiation source to an array of optical transceiver cells. Optical delay lines in these embodiments can be coupled to one or more of the optical networks in order to delay a given portion of the coherent radiation relative to another.

Transceiver Arrays for Multi-Wavelength Scanning

In some applications of coherent sensing and optical transceiver arrays, a target is scanned at multiple different wavelengths. In some cases, it is desirable that all the wavelengths be scanned simultaneously, rather performing multiple scans over the target at different wavelengths. The embodiments that are described above can be adapted for this purpose by incorporating multiple distribution trees in the optical sensing device. The distribution trees convey coherent radiation to the transceiver cells in different, respective wavelength bands. Thus, coherent radiation in the different wavelength bands can be conveyed simultaneously over the different distribution trees to different, respective sets of the optical transceiver cells. The radiation in the multiple wavelength bands is coupled between the optical transducers and the target, so that the sets of optical transceiver cells sense different wavelength bands in each scan.

This approach can be useful in applications that call for wideband sensing, such as in OCT. For this purpose, OCT systems that are known in the art typically use laser sources having a broad spectral band or a broad spectral scanning range—typically in excess of 100 nm. Such laser sources are costly and consume substantial space. In addition, it is difficult to optimize the elements of a PIC for such a wide wavelength range.

An embodiment of the present invention offers a less costly and more compact alternative, based on multiple laser sources operating in different, adjacent wavelength bands. The sensing system in this case directs each wavelength band to a different, respective set of optical transceiver cells. The coherent radiation output by each laser source may have a large bandwidth, covering the respective wavelength band, or the wavelength of each laser source may be scanned over the respective wavelength band. A processor combines and stitches together the signals received from the transceiver cells in the different wavelength bands and thus computes a high-resolution depth map. In this manner, the system is able to achieve the resolution of an OCT scan made using a single broadband coherent source, while using multiple solid-state laser sources, such as semiconductor lasers, with much narrower bandwidths, lower cost, and smaller size.

Thus, in the present embodiments, an optoelectronic device comprises an array of optical transceiver cells on a substrate, partitioned into multiple disjoint sets, for example, two, three, or more sets. Waveguides on the substrate define multiple optical networks, which convey coherent radiation from respective radiation sources in different, respective wavelength bands to the optical transceiver cells in each of the sets, respectively. In other words, each set of optical transceiver cells receives coherent radiation in a different, respective wavelength band from the optical network to which it is connected.

An optical transducer in each optical transceiver cell couples a portion of the coherent radiation in the respective wavelength band toward a target and receives optical radiation reflected from the target. A receiver in the optical transceiver cell mixes the received optical radiation with another (LO) portion of the coherent radiation in the same wavelength band and outputs an electrical signal in response to the mixed radiation. A scanner scans the fields of view of the optical transceiver cells over the target, such that each area of the target is swept sequentially by at least one transceiver cell in each set. For this purpose, for example, the sets of transceiver cells can be arranged in respective columns of the array, extending along respective, parallel column axes, which are perpendicular to the direction of the scan.

Figure 12:
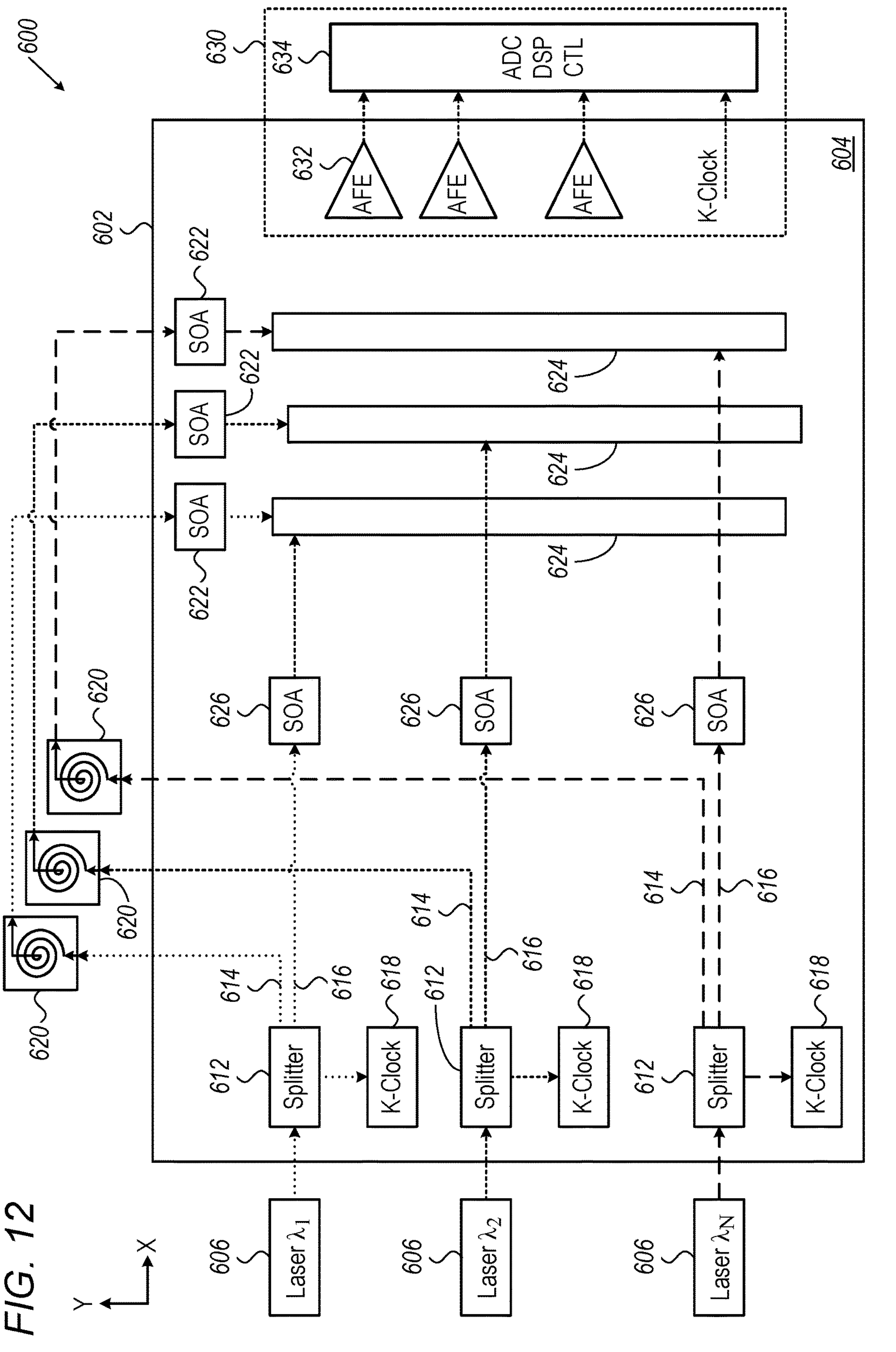
FIG. 12 is a block diagram that schematically illustrates an optical sensing system, in accordance with still another embodiment of the invention.

FIG. 12 is a block diagram that schematically illustrates an optical sensing system 600, in accordance with yet another embodiment of the invention. System 600 comprises a coherent optical sensing device 602, implemented on a PIC 604. Device 602 is similar in its construction and principles of operation to the systems described above, but comprises multiple separate wavelength channels, each fed by a respective laser light source 606. The laser light sources output modulated coherent radiation in respective frequency bands $\lambda_1, \lambda_2, \ldots, \lambda_N$, which may be disjoint or overlapping. In one embodiment, the laser wavelengths are swept across the respective bands, and system 600 collects signals as a function of optical wavelength or frequency in the course of each scan. Although three laser light sources 606 are shown in FIG. 12, along with the corresponding channels in device 602, the principles of the present embodiment may similarly be applied in systems comprising smaller or larger numbers of light sources and channels.

A respective splitter 612 splits the coherent radiation at each wavelength between a reference arm 614, a signal arm 616, and a calibration unit 618. Calibration units 618 extract phase-synchronized K-clocks from the wavelength-swept beams in order to synchronize the measurements made by device 602 in the frequency domain, as described further hereinbelow.

The beam in each reference arm 614 is routed through an optical distribution tree that includes a respective delay line 620 in the LO beam path for each wavelength channel. Delay lines 620 may be implemented off PIC 604, for example using fiberoptics, or on PIC 604 using suitable waveguides. As in the preceding embodiments, delay lines 620 may apply either fixed or adjustable delays. For each wavelength channel, a respective optical switch network 622 distributes the LO beam among a group 624 of transceiver cells. For the sake of simplicity, each network 622 is represented in FIG. 12 by a single "SOA," with a single output to the entire group of transceiver cells. Although this mode of operation is possible, with a single column of transceiver cells receiving the amplified LO beam during an entire scan over a target, each network 622 may more generally comprise a more complex network of switches, which selectively actuated different sets of transceiver cells within the corresponding group 624, for example as shown in the preceding embodiments.

The beam in each signal arm 616 is routed by an optical switch network 626 to the same set of transceiver cells in group 624 as the LO beam. The selected transceiver cells transmit the beams provided by network 626 toward the target and then receive radiation reflected from the target and mix the received radiation with the LO beams provided by network 622. By selective activation of different transceiver cells at different times, system 600 is able to cover a large area of the target with high throughput while avoiding interference that might otherwise arise between neighboring transceiver cells.

As in the preceding embodiments (for example as shown in FIG. 3), the transceiver cells in groups 624 each comprise an optical transducer, which couples the portion of the coherent radiation delivered by network 626 toward a target external to the substrate and receives optical radiation reflected from the target. A receiver in each transceiver cell mixes the optical radiation received by the optical transducer with the portion of the coherent radiation delivered by network 622 and outputs an electrical signal responsively to the mixed radiation.

Typically, a scanner (as shown in FIG. 1 or 5A, for example), scans the fields of view of the transceiver cells over the target. The set of transceiver cells to activate in each group is selected so that in the course of the scan, each point on the target is sensed in succession at each of wavelengths $\lambda_1, \lambda_2, \ldots, \lambda_N$. For example, assuming the selected set of transceiver cells in each group 624 to be arranged in a column along the Y-direction, and the scan to be carried out in the X-direction, the scanner will sweep the fields of view of the transceiver cells in each of the columns will sweep across the target in succession.

The electrical signals output by the transceiver cells are conveyed to an electronic processing unit 630, which includes an analog front end (AFE) 632 and a digital processing block 634. Digital processing block 634 typically includes an ADC and a DSP, which processes the signals to extract data, such as depth information, along with a controller, such as processor 48. For OCT processing, the DSP typically collects data samples as a function of frequency in all the wavelength channels and transforms the collected samples to the spatial domain in order to reconstruct a 3D image of the target, over the signals output by the transceiver cells in the different, respective wavelength bands.

For accurate 3D reconstruction, the phase-synchronized K-clocks generated by calibration units 618 are applied to ensure that the samples are uniformly separated and mutually aligned in frequency space. For this purpose, the calibration units comprise at least one interferometric optical circuit, which extracts respective K-clocks from the coherent radiation emitted by laser light sources 606 in the respective wavelength bands. Digital processing block 634 synchronizes the signals output by the optical transceiver cells in the different wavelength channels using the respective K-clocks. This functionality is described further hereinbelow.

FIG. 13 is a block diagram that schematically illustrates the operation of calibration unit 618, in accordance with an embodiment of the invention. Calibration unit 618 in this embodiment comprises a K-clock detector 640, a line trigger detector 642, and optionally a power monitor 644. A beamsplitter 646 divides the beam provided by laser source 606 among these components. Laser source 606 is modulated to sweep its wavelength over a specified frequency range. Typically, however, the frequency sweep is not precisely linear over time, and laser beam power may vary across the spectrum, as well. Calibration unit 618 detects these frequency and power variations so that digital processing block 634 can correct the signals accordingly.

K-clock detector 640 comprises an interferometric optical circuit, including a Mach-Zehnder interferometer 648 with a long reference arm (for example, 1-100 mm delay) and a large frequency spectral range (FSR) (for example about 1-100 GHz). As the frequency of laser source 606 is swept, interferometer 648 generates an optical output comprising peaks that are equally spaced in optical frequency (k-space), corresponding the zero-crossings of the interference fringe signals. A photodetector 650, such as a balanced photodiode pair, outputs an electrical signal corresponding to the interferometer output, and a clock generator 652 outputs a sequence of pulses corresponding to the zero-crossing times. Alternatively, other detection techniques, such as I/Q detection, can be used to improve the precision and performance of the K-clock.

Line trigger detector 642 is used to detect a reference frequency in the spectrum. In the pictured example, detector 642 comprises an integrated Bragg grating (IBG) 654 on PIC 604, which serves as a sharp notch filter, creating a sharp reflection peak at a selected wavelength. A directional coupler 656 conveys this reflection to a voltage-biased (VB) photodiode circuit 658. IBG 654 is terminated in this example by a photodiode 660 which can be used to monitor the performance of line trigger detector 642, as well as the power of the laser source. A line trigger generator 662 outputs a pulse each time the wavelength of laser source 606 passes through the notch wavelength of IBG 654.

Additionally or alternatively, a monitoring photodiode 662 in power monitor 644 measures the laser power as a function of frequency. Alternatively, for greater accuracy, each transceiver cell or optical bus has its own monitoring photodiode for this purpose.

FIGS. 14A, 14B, and 14C are spectral plots that schematically illustrate the operation of calibration unit 618, in accordance with an embodiment of the invention. FIG. 14A shows the output spectrum over which laser source 606 is swept. The power of the coherent radiation output by the laser varies as a function of wavelength. (In addition, as noted above, although it is desirable that the frequency of the radiation be swept linearly over time, in practice the sweep typically has some nonlinearity.)

FIG. 14B shows the spectrum of the radiation that is transmitted through IBG 654 to photodiode 660, while FIG. 14C shows the notch spectrum that is reflected by IBG 654 back to photodiode circuit 658. Each time the wavelength of laser source 606 sweeps through the notch wavelength AB, line trigger generator 662 will output a corresponding trigger pulse.

In the scheme shown in FIG. 12, each wavelength channel has its own calibration unit 618, which generates a corresponding K-clock and line trigger, as explained above. Process and operational variations in device 602, however, may cause an FSR mismatch between channels. Furthermore, the relative frequencies of the channels may drift during operation. Therefore, in some embodiments, a global reference unit is used, in addition to the individual single-channel calibration units 618, to maintain calibration between the different wavelength channels and specifically to normalize the K-clocks, power, and reference triggers of the channels.

Figure 15:
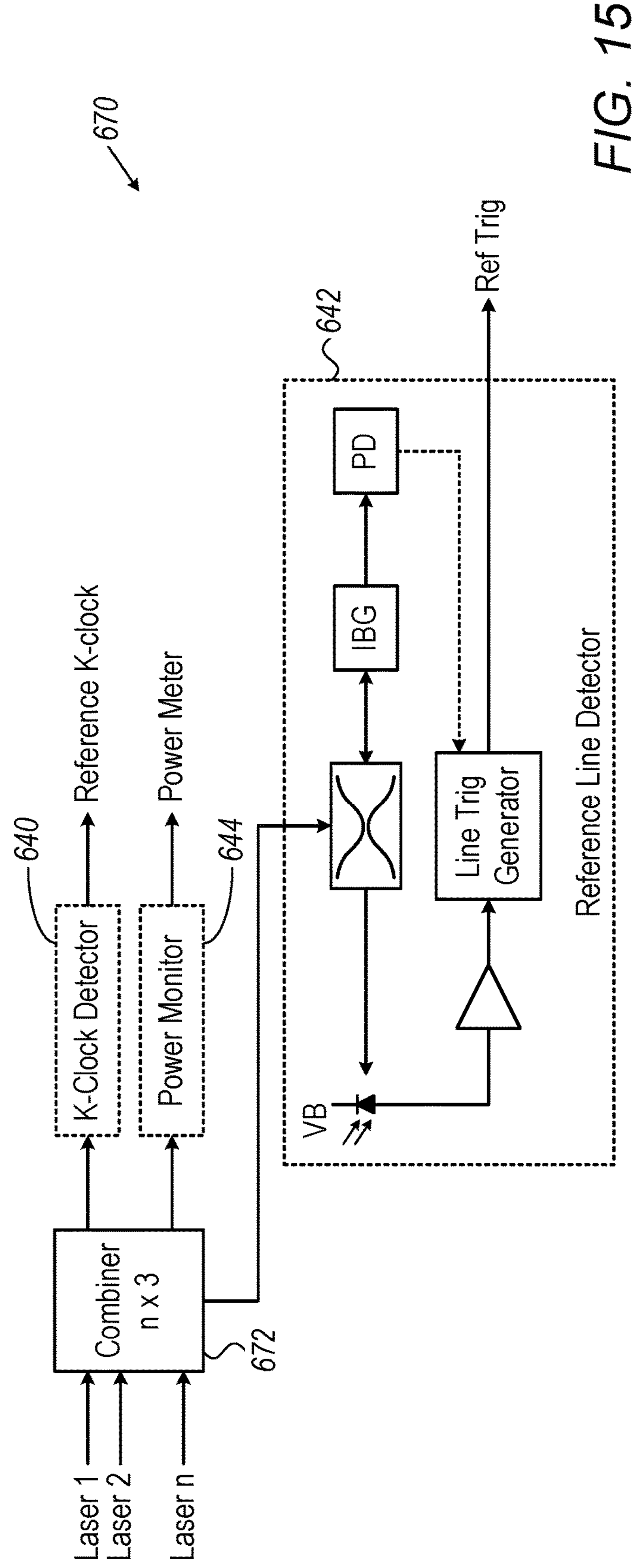
FIG. 15 is a block diagram that schematically illustrates a global reference unit, in accordance with an embodiment of the invention.

FIG. 15 is a block diagram that schematically illustrates a global reference unit 670 that can be used for this purpose, in accordance with an embodiment of the invention. Unit 670 a shared K-clock detector 640 and line detector 642, as well as a shared power monitor 644. A combiner 672 receives a portion of the coherent radiation output by each of the laser sources and selects the laser sources sequentially for input to global reference unit 670 during a calibration phase. In one embodiment, active photonic switches can be used in combiner 672 to select the laser source of interest subsequently during normal operation of the system to avoid interfering with the operation of the other laser sources. Alternatively, combiner 672 may comprise passive components, in which case each laser source can be switched on in turn and swept across its wavelength range to estimate a global K-clock and compare it with the corresponding K-clock generated by the respective calibration unit 618.

Figure 16:
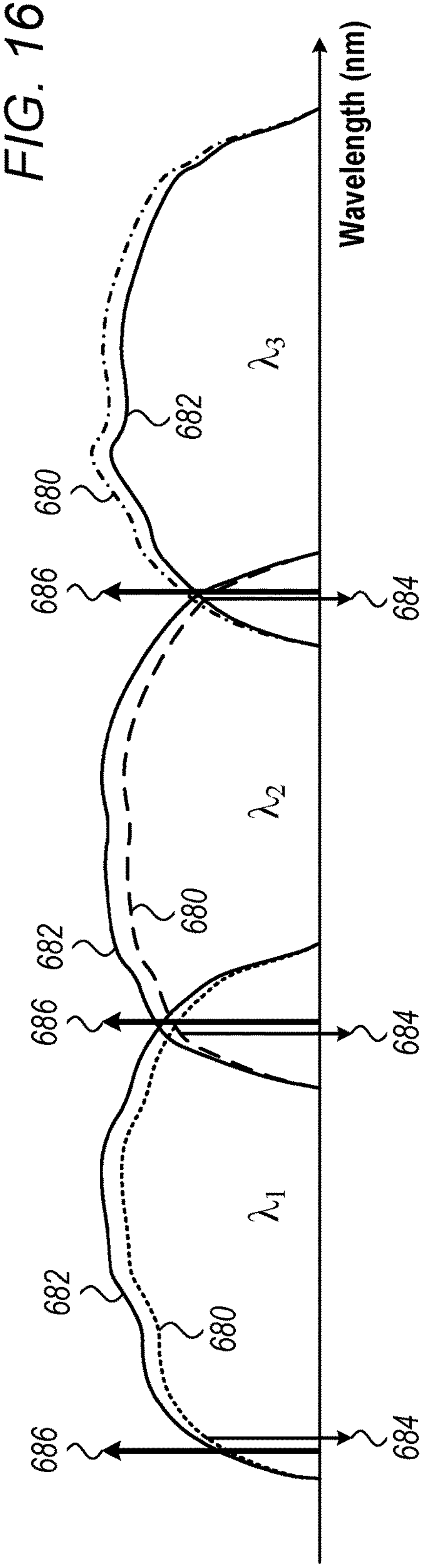
FIG. 16 is a spectral diagram that schematically illustrates signals generated by calibration units and a global reference unit, in accordance with an embodiment of the invention.

FIG. 16 is a spectral diagram that schematically illustrates signals generated by calibration units 618 and global reference unit 670, in accordance with an embodiment of the invention. The measurements are made in three wavelength bands $\lambda_1$, $\lambda_2$, $\lambda_3$, which are generated by corresponding laser sources 606. Power monitors 644 in calibration units 618 generate respective output curves 680, which are compared to a global output curve 682. Digital processing block 634 calibrates each of the channels to correct for the mismatch between curves 680 and 682 and uses the calibration in normalizing the amplitudes of the samples that it receives from the transducer cells in the corresponding groups 624.

In addition, digital processing block 634 senses line triggers 684 that are output by the respective line trigger detectors 642 in calibration units 618 to line triggers 686 that are output by global reference unit 670. Specifically, digital processing block 634 will calibrate and apply a respective frequency offset in each wavelength band to compensate for the mismatch between triggers 684 and 686.

Finally, digital processing block 634 will compare the K-clocks output by K-clock detectors 640 in calibration units 618 and will resample and adjust the clock frequencies to compensate for the differences.

Figure 17:
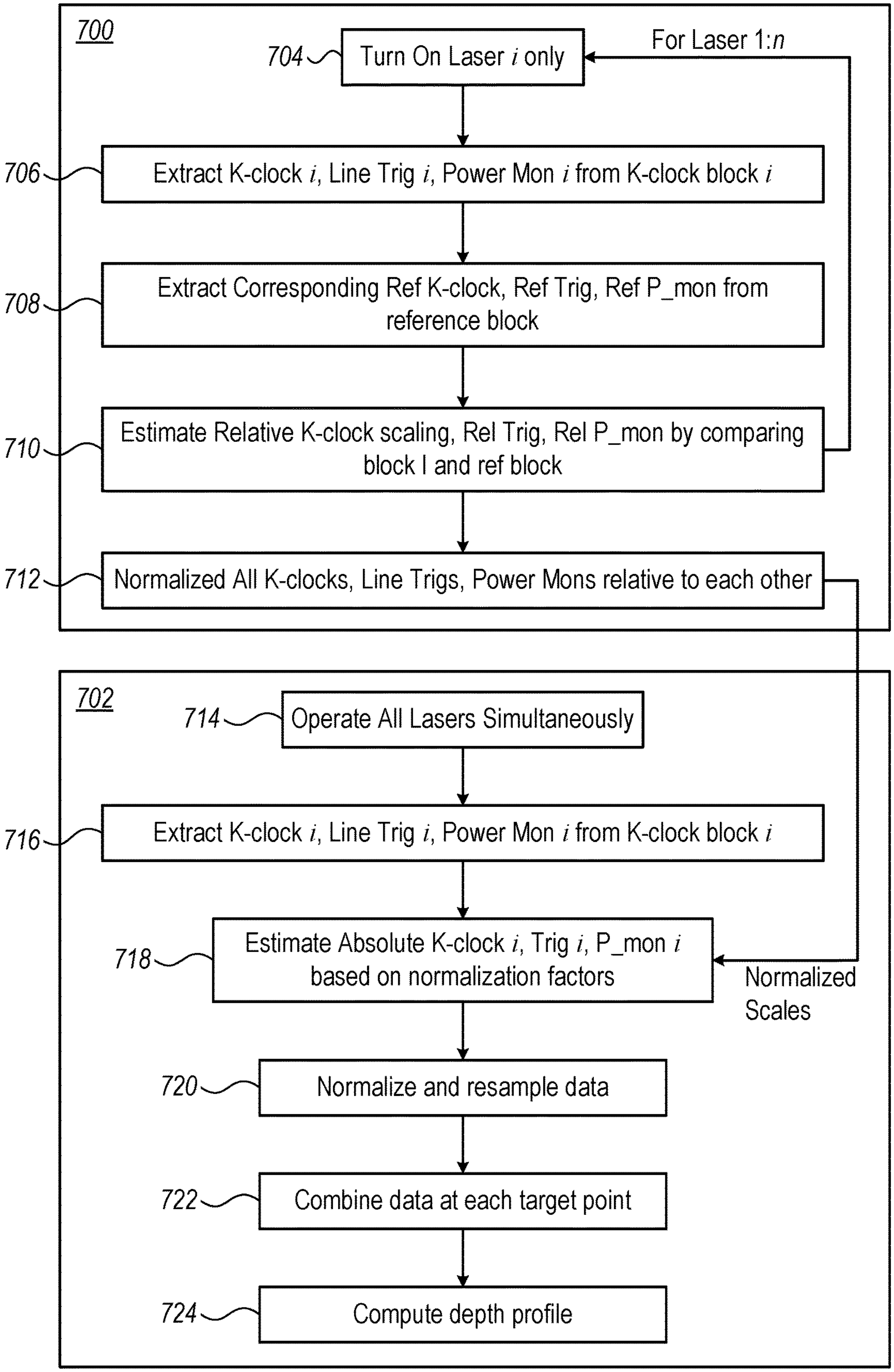
FIG. 17 is a flow chart that schematically illustrates a method for calibration and data processing using K-clocks, in accordance with an embodiment of the invention.

FIG. 17 is a flow chart that schematically illustrates a method for calibration and data processing using K-clocks, in accordance with an embodiment of the invention. This method is described, for the sake of clarity, with reference to the elements of system 600 and calibration units 618 and 670, as described above. Alternatively, the method may be applied, mutatis mutandis, in other sorts of multi-channel systems in which multiple swept-wavelength laser sources are used.

The method of FIG. 17 comprises a pre-operational calibration phase 700, followed by a measurement phase 702. In the course of calibration phase 700, each laser source is turned on individually, in an actuation step 704. Digital processing block 634 receives the K-clock, line trigger, and power measurement extracted by the corresponding calibration unit 618, at a channel measurement step 706. Digital processing block 634 also receives the K-clock, line trigger, and power measurement extracted by global reference unit 670, at a global measurement step 708. Digital processing block 634 compares the values extracted at steps 706 and 708 to derive respective scaling and calibration factors for each wavelength channel, at a calibration step 710. Once the scaling and calibration factors have been computed for all the individual channels, digital processing block 634 computes normalization factors for all channels, at a normalization step 712. These normalization factors enable the digital processing block to normalize the K-clocks, line triggers, and power levels of all the channels to a common scale.

In measurement phase 702, all of laser sources 606 are actuated simultaneously, at an actuation step 714. The fields of view of the transceiver cells are scanned, as explained above, so that each target point is sensed successively by a transceiver cell in each of the wavelength bands. While acquiring data from the transceiver cells, digital processing block 634 also receives the K-clocks, line triggers, and power measurements extracted by calibration units 618 for all the wavelength channels, at a channel monitoring step 716. For each wavelength channel, digital processing block 634 applies the normalization factors derived at step 712 is correcting the current channel parameters, thus estimating the absolute values of the K-clock, line trigger, and power level for the channel, at a parameter correction step 718.

Using the corrected channel parameters, digital processing block 634 resamples and normalizes the data acquired from the transceiver cells, at a data correction step 720. The normalized samples from each channel are converted to the frequency domain using the frequency values indicated by the corresponding corrected K-clock. Using the known scanning speed, digital processing block 634 combines the frequency-domain data acquired by the transceiver cells in the different wavelength channels, at a data combination step 722. In other words, for each point on the target, the digital processing block identifies the time during the scan at which the point was within the field of view of a respective transceiver cell in each of the wavelength channels and extracts the normalized frequency-domain data acquired at the time.

Thus, for each such point, digital processing block 634 acquires and stitches together the frequency-domain data across all the wavelength bands into a single, synchronized spectrum, as though the data had been acquired by a single broadband detector, rather than by multiple different transceiver cells at different wavelengths and in different time windows. The digital processing block filters and transforms the frequency-domain data to the spatial domain, using a Fast Fourier Transform (FFT), for example, in order to compute a depth map of the target, at a depth profiling step 724.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An optoelectronic device, comprising:

a planar substrate;

an array of optical transceiver cells disposed on the substrate, each transceiver cell comprising an optical transducer configured to couple optical radiation between the transceiver cell and a target external to the substrate;

an optical distribution tree, comprising a network of waveguides and switches disposed on the substrate, coupled to convey coherent radiation from a radiation source to the optical transceiver cells, wherein the optical distribution tree comprises multiple passive splitters, which divide the coherent radiation among the waveguides constituting branches of the tree, and wherein the switches comprise semiconductor optical amplifiers (SOAs), which are coupled between one or more of the passive splitters and the waveguides constituting the branches of the tree; and a controller, which is configured to actuate the switches by actuating and deactuating the SOAs so as to select different subsets of the optical transceiver cells that are to receive the coherent radiation from the optical distribution tree and to transmit the coherent radiation toward the target at different times during a scan of the target.

2. The device according to claim 1, wherein the transceiver cells have respective fields of view, which are defined by respective optical apertures of the optical transducers, and wherein the device comprises a scanner, which is configured to scan the fields of view over the target.

3. The device according to claim 2, wherein as the scanner scans the fields of view over the target, the optical apertures define respective scan lines extending along a scan direction of the scanner, and wherein the controller is configured to actuate the switches so as to select the scan lines to be probed by the device.

4. The device according to claim 1, wherein the optical distribution tree comprises multiple optical buses, wherein each optical bus is coupled to receive the coherent radiation from a respective one of the SOAs and to distribute the coherent radiation among a respective group of the optical transceiver cells.

5. The device according to claim 4, wherein each of the optical transceiver cells comprises at least one tap coupled to extract a portion of the coherent radiation propagating through the optical bus for transmission of the coherent radiation via the optical transducer.

6. The device according to claim 1, wherein each optical transceiver cell comprises a receiver, which is coupled to mix a local part of the coherent radiation conveyed from the optical distribution tree to the optical transceiver cell with the optical radiation received by the optical transducer and to output an electrical signal responsively to the mixed radiation.

7. The device according to claim 1, wherein the optical distribution tree comprises at least first and second trees, which are coupled to convey the coherent radiation in at least first and second wavelength bands, respectively, to at least first and second sets of the optical transceiver cells simultaneously for coupling between the optical transceiver cells and the target.

8. An optoelectronic device, comprising:

a planar substrate;

an array of optical transceiver cells disposed on the substrate, each transceiver cell comprising an optical transducer configured to couple optical radiation between the transceiver cell and a target external to the substrate;

an optical distribution tree, comprising a network of waveguides and switches disposed on the substrate, coupled to convey coherent radiation from a radiation source to the optical transceiver cells; and a controller, which is configured to actuate the switches so as to select different subsets of the optical transceiver cells that are to receive the coherent radiation from the optical distribution tree and to transmit the coherent radiation toward the target at different times during a scan of the target;

wherein each optical transceiver cell comprises a receiver, which is coupled to mix a local part of the coherent radiation conveyed from the optical distribution tree to the optical transceiver cell with the optical radiation received by the optical transducer and to output an electrical signal responsively to the mixed radiation, and wherein the optical distribution tree comprises:

a first tree coupled to convey a first portion of the coherent radiation from the radiation source to the optical transceiver cells for transmission via the optical transducer toward the target; and a second tree coupled to convey a second portion of the coherent radiation from the radiation source to the optical transceiver cells to serve as the local part for mixing with the received optical radiation.

9. The device according to claim 8, wherein the second tree comprises at least one optical delay line, configured to delay the second portion of the coherent radiation relative to the first portion.

10. The device according to claim 9, wherein the at least one delay line is configured to apply an adjustable delay to the second portion of the coherent radiation, and wherein the controller is configured to set the adjustable delay responsively to a range of distances from the device to the target that is to be probed by the optical transceiver cells.

11. The device according to claim 6, wherein the signal output by the receiver in each transceiver cell comprises a beat frequency responsive to a range of the target from the device.

12. The device according to claim 8, wherein the controller is configured to actuate the switches in both the first and second trees so that the optical transceiver cells in the selected subsets receive the coherent radiation simultaneously from both the first and second trees.

13. A method for sensing, comprising:

providing an array of optical transceiver cells disposed on a substrate, each transceiver cell comprising an optical transducer configured to couple optical radiation between the transceiver cell and a target external to the substrate;

coupling an optical distribution tree, comprising a network of waveguides and switches disposed on the substrate, to convey coherent radiation from a radiation source to the optical transceiver cells, wherein the optical distribution tree comprises multiple passive splitters, which divide the coherent radiation among the waveguides constituting branches of the tree, and wherein the switches comprise semiconductor optical amplifiers (SOAs), which are coupled between one or more of the passive splitters and the waveguides constituting the branches of the tree; and actuating the switches by actuating and deactuating the SOAs so as to select different subsets of the optical transceiver cells that are to receive the coherent radiation from the optical distribution tree and to transmit the coherent radiation toward the target at different times during a scan of the target.

14. The method according to claim 13, wherein the optical distribution tree comprises multiple optical buses, wherein each optical bus is coupled to receive the coherent radiation from a respective one of the SOAs and to distribute the coherent radiation among a respective group of the optical transceiver cells.

15. The method according to claim 14, wherein each of the optical transceiver cells comprises at least one tap coupled to extract a portion of the coherent radiation propagating through the optical bus for transmission of the coherent radiation via the optical transducer.

16. The method according to claim 13, wherein each optical transceiver cell comprises a receiver, which is coupled to mix a local part of the coherent radiation conveyed from the optical distribution tree to the optical transceiver cell with the optical radiation received by the optical transducer and to output an electrical signal responsively to the mixed radiation.

17. The method according to claim 16, wherein coupling the optical distribution tree comprises:

coupling a first tree to convey a first portion of the coherent radiation from the radiation source to the optical transceiver cells for transmission via the optical transducer toward the target; and coupling a second tree to convey a second portion of the coherent radiation from the radiation source to the optical transceiver cells to serve as the local part for mixing with the received optical radiation.

18. The method according to claim 17, wherein actuating the switches comprises actuating the switches in both the first and second trees so that the optical transceiver cells in the selected subsets receive the coherent radiation simultaneously from both the first and second trees.

19. The method according to claim 17, wherein coupling the second tree comprises connecting at least one optical delay line to delay the second portion of the coherent radiation relative to the first portion.

20. The method according to claim 19, wherein connecting the at least one delay line comprises applying an adjustable delay to the second portion of the coherent radiation, and setting the adjustable delay responsively to a range of distances to the target that is to be probed by the optical transceiver cells.

21. The method according to claim 16, wherein the signal output by the receiver in each transceiver cell comprises a beat frequency responsive to a range of the target from the optical transceiver cells.

22. The method according to claim 13, wherein the transceiver cells have respective fields of view, which are defined by respective optical apertures of the optical transducers, and wherein the method comprises scanning the fields of view over the target.

23. The method according to claim 22, wherein scanning the fields of view comprises defining respective scan lines extending along a scan direction, and wherein actuating the switches comprises selecting the scan lines to be probed by the fields of view.

24. The method according to claim 13, wherein coupling the optical distribution tree comprises coupling at least first and second trees to convey the coherent radiation in at least first and second wavelength bands, respectively, to at least first and second sets of the optical transceiver cells simultaneously for coupling between the optical transceiver cells and the target.

* * * * *